US011819535B2

(12) United States Patent
Liu et al.

(10) Patent No.: US 11,819,535 B2
(45) Date of Patent: Nov. 21, 2023

(54) COMPOSITION AND METHODS FOR REGULATING EXTRACELLULAR MATRIX ACCUMULATION

(71) Applicant: UNIVERSITY HEALTH NETWORK, Toronto (CA)

(72) Inventors: Fei-Fei Liu, Toronto (CA); Xiao Zhao, Toronto (CA); Kenneth W. Yip, Toronto (CA)

(73) Assignee: UNIVERSITY HEALTH NETWORK, Toronto (CA)

( * ) Notice: Subject to any disclaimer, the term of this patent is extended or adjusted under 35 U.S.C. 154(b) by 208 days.

(21) Appl. No.: 16/442,110

(22) Filed: Jun. 14, 2019

(65) Prior Publication Data

US 2019/0381133 A1   Dec. 19, 2019

Related U.S. Application Data

(60) Provisional application No. 62/685,076, filed on Jun. 14, 2018.

(51) Int. Cl.
*A61K 45/06* (2006.01)
*A61P 17/00* (2006.01)
*A61K 39/00* (2006.01)
*A61K 38/17* (2006.01)

(52) U.S. Cl.
CPC .......... *A61K 38/1774* (2013.01); *A61K 39/00* (2013.01); *A61K 45/06* (2013.01); *A61P 17/00* (2018.01)

(58) Field of Classification Search
None
See application file for complete search history.

(56) References Cited

U.S. PATENT DOCUMENTS

2016/0279130 A1* 9/2016 Zemel .................... A61K 45/06

OTHER PUBLICATIONS

Anantharaju et al. An overview on the role of dietary phenolics for the treatment of cancers. Nutrition Journal (2016) 15:99.*
Reyes et al. Caffeic acid prevents liver damage and ameliorates liver fibrosis induced by CCI4 in the rat. Drug Development Research 36:125-128 (1995).*
Chen et al. Caffeic acid phenethyl ester decreases acute pneumonitis after irradiation in vitro and in vivo. BMC Cancer 2005, 5:158.*
Song et al. The Effect of Caffeic Acid on Wound Healing in Skin-incised Mice. Korean J Physiol Pharmacol, vol. 12: 343-347, Dec. 2008.*
Artlett C. M. Inflammasomes in wound healing and fibrosis. J Pathol 2013; 229: 157-167.*
Jacobson et al. Impaired wound healing after radiation therapy: A systematic review of pathogenesis and treatment. JPRAS Open 13 (2017), 92-105. Published online Jun. 9, 2017.*
Watt, Fiona M.; Mammalian skin cell biology: At the interface between laboratory and clinic; SCIENCE sciencemag.org; Nov. 21, 2014 • vol. 346 Issue 6212; Science 346 (6212), pp. 937-940. DOI: 10 1126/science. 1253734; Science (print ISSN 0036-8075; online ISSN 1095-9203) is published by the American Association for the Advancement of Science, Washington, DC.
Heiden, Matthew G. Vander et al.; Understanding the Warburg Effect: The Metabolic Requirements of Cell Proliferation; www.sciencemag.org SCIENCE vol. 324 May 22, 2009; Science 324 (5930), pp. 1029-1033. DOI: 10.1126/science.1160809; Science (print ISSN 0036-8075; online ISSN 1095-9203) is published by the American Association for the Advancement of Science, Washington, DC.
Kelly, Beth and O'Neill, Luke AJ; Metabolic reprogramming in macrophages and dendritic cells in innate immunity; Cell Research (2015) 25: pp. 771-784. DOI: 10.1038/cr.2015.68; published online Jun. 5, 2015; Cell Research (2015) 25:771-784. www.nature.com/cr.
Stone, Helen B et al; Effects of radiation on normal tissue: consequences and mechanisms; THE LANCET Oncology vol. Sep. 4, 2003 http://oncology.thelancet.com; Lancet Oncol 2003; 4: pp. 529-536.
Kok, Helena M et al; Targeting CTGF, EGF and PDGF pathways to prevent progression of kidney disease; Nat. Rev. Nephrol. 10, pp. 700-711 (2014); published online Oct. 14, 2014; D0I:10.1038/nrneph.2014.184; www.nature.com/reph.
Higgins, Debra F. et al; Hypoxic induction of CTGF is directly mediated by Hif-1; Am J Physiol Renal Physiol 287: pp F1223-F1232, 2004. First published Aug. 17, 2004; DOI:10.1152/ajprenal. 00245 2004.; Downloaded from journals.physiology.org/journal/ajprenal at University Health Network (205.189.058.082) on Jun. 12, 2020. http://www.ajprenal.org.
Lamb, Justin et al; The Connectivity Map: Using Gene-Expression Signatures to Connect Small Molecules, Genes, and Disease; www.sciencemag.org SCIENCE vol. 313 Sep. 29, 2006; Science 313 (5795), pp. 1929-1935. DOI: 10.1126/science.1132939.
Vanella, Luca et al; Caffeic Acid Phenethyl Ester Regulates PPAR's Levels in Stem Cells-Derived Adipocytes; Hindawi Publishing Corporation PPAR Research vol. 2016, Article ID 7359521, pp. 1-13 http://dx.doi.org/10.1155/2016/7359521.
Isono, Motohide et al; Smad pathway is activated in the diabetic mouse kidney and Smad3 mediates TGF-p-induced fibronectin in mesangial cells; Biochemical and Biophysical Research Communications 296 (2002) pp. 1356-1365 www. academicpre ss. com; PII S0006-291X(02)02084-3.
McCulloch, Christopher A.G. and Knowles, Gisele C.; Deficiencies in Collagen Phagocytosis by Human Fibroblasts In Vitro: A Mechanism for Fibrosis?; Journal of Cellular Physiology 155: pp. 461-471 (1993).
Febbraio, Maria et al; CD36: a class B scavenger receptor involved in angiogenesis, atherosclerosis, inflammation, and lipid metabolism; JCI The Journal of Clinical Investigation; J Clin Invest. 2001 ;108(6): pp. 785-791. https://doi.org/10.1172/JCI14006.

(Continued)

*Primary Examiner* — Nianxiang Zou
(74) *Attorney, Agent, or Firm* — Norton Rose Fulbright Canada LLP

(57) ABSTRACT

There is described herein methods of treating a disease associated with extracellular matrix (ECM) in a patient. In some cases, the methods comprise administering to the patient a therapeutically effective amount of fibroblasts which express CD36.

4 Claims, 25 Drawing Sheets

(56) References Cited

OTHER PUBLICATIONS

Zhang, Pengxuan et al; Bioactivity and Chemical Synthesis of Caffeic Acid Phenethyl Ester and Its Derivatives; Molecules 2014, 19, pp. 16458-16476; DOI:10.3390/moleculesl91016458; ISSN 1420-3049 www.mdpi.com/journal/molecules.

Doburn, Chris T. et al; Defective Uptake and Utilization of Long Chain Fatty Acids in Muscle and Adipose Tissues of CD36 Knockout Mice; The Journal of Biological Chemistry; vol. 275, No. 42, Issue of Oct. 20, 2000, pp. 32523-32529, and in revised form, Jun. 26, 2000 Published, JBC Papers in Press, Jul. 25, 2000, DOI: 10.1074/jbc.M003826200.

Vincent, Annette S. et al; Human Skin Keloid Fibroblasts Display Bioenergetics of Cancer Cells; Journal of Investigative Dermatology (2008) 128, pp. 702-709; DOI:10.1038/sj.jid.5701107; published online Oct. 18, 2007.

Ring, Axel et al; Caveolin-1 is required for fatty acid translocase (FAT/CD36) localization and function at the plasma membrane of mouse embryonic fibroblasts; Biochimica et Biophysica Acta 1761 (2006) pp. 416-423; http://www.elsevier.com/locate/bba.

Del Galdo, Francesco et al; Decreased Expression of Caveolin 1 in Patients With Systemic Sclerosis Crucial Role in the Pathogenesis of Tissue Fibrosis; ARTHRITIS & RHEUMATISM vol. 58, No. 9, Sep. 2008, pp. 2854-2865 DOI: 10.1002/art .23791 © 2008, American College of Rheumatology.

Castello-Cros; Remedios et al; Scleroderma-like properties of skin from caveolin-1-deficient mice; Cell Cycle 10:13, pp. 2140-2150; Jul. 1, 2011; © 2011 Landes Bosciencehttps://doi.Org/10.4161 /cc.10.13.16227; ISSN: 1538-4101 (Print) 1551-4005 (Online) Journal homepage: https://www.tandfonline.com/loi/kccy20.

Xie, Na et al; Glycolytic Reprogramming in Myofibroblast Differentiation and Lung Fibrosis; American Journal of Respiratory and Critical Care Medicine vol. 192 Number 12 | Dec. 15, 2015; Am J Respir Grit Care Med vol. 192, Iss 12, pp. 1462-1474, Dec. 15, 2015; DOI: 10.1164/rccm.201504-0780CC on Aug. 18, 2015.

Kang, Hyun Mi et al; Defective fatty acid oxidation in renal tubular epithelial cells has a key role in kidney fibrosis development; Nature Medicine vol. 21 | No. | Jan. 2015; pp. 37-47; DOI:10.1038/nm.3762.

Lovisa, Sara et al; Partial Epithelial-to Mesenchymal Transition and Other New Mechanisms of Kidney Fibrosis Trends in Endocrinology & Metabolism, Oct. 2016, vol. 27, No. 10 ; pp. 681-695; http://dx.doi.Org/10.1016/j.tem.2016.06.004.

Stone, Helen B.; Leg Contracture in Mice: An Assay of Normal Tissue Response; Int. J. Radiation Oncology Biol. Phys. vol. 10, pp. 1053-1061; Radiation Oncology • Biology • Physics Jul. 1984, vol. 10, No. 7.

Trapnell, Cole et al; Differential gene and transcript expression analysis of RNA-seq experiments with TopHat and Cufflinks; vol. 7 No. 3 | 2012 | NATURE PROTOCOLS; pp. 562-579; Published online Mar. 1, 2012; corrected after print Aug. 7, 2014; doi:10.1038/nprot.2012.016.

Dutta, Tumpa et al; Concordance of Changes in Metabolic Pathways Based on Plasma Metabolomics and Skeletal Muscle Transcriptomics in Type 1 Diabetes; diabetes, diabetes) oumals. org ; DIABETES, vol. 61, May 2012; pp. 1004-1016; DOI: 10.2337/dbl 1-0874.

Pfaffl, Michael W et al.; Relative expression software tool (REST) for group-wise comparison and statistical analysis of relative expression results in real-time PCR; Nucleic Acids Research, 2002 vol. 30 No 9 e36; pp. 1-13.

Ran, F Ann et al; Genome engineering using the CRISPR-Cas9 system; Nature Protocols | vol. 8 No. 11 | 2013 pp. 2281-2308; Published online Oct. 24, 2013; DOI:10.1038/nprot.2013.143.

Dennler, Sylviane et al; Direct binding of Smad3 and Smad4 to critical TGFp-inducible elements in the promoter of human plasminogen activator inhibitor-type 1 gene; The EMBO Journal vol. 17 No. 11 pp. 3091-3100, 1998.

Rizarry, Rafael A et al; Exploration, normalization, and summaries of high density oligonucleotide array probe level data; Biostatistics (2003), 4,2, pp. 249-264.

Smirnov, Petr et al; PharmacoGx: an R package for analysis of large pharmacogenomic datasets; Bioinformatics, 32(8), 2016, pp. 1244-1246 DOI: 10.1093/bioinformatics/btv723 Advance Access Publication Date: Dec. 9, 2015.

Rousseeuw, Peter J.; Silhouettes: a graphical aid to the interpretation and validation of cluster analysis; Journal of Computational and Applied Mathematics 20 (1987) pp. 53-65 North-Holland.

\* cited by examiner

COMPOSITION AND METHODS FOR REGULATING EXTRACELLULAR MATRIX ACCUMULATION

CROSS-REFERENCE TO RELATED APPLICATIONS

This application claims priority to U.S. Provisional Application No. 62/685,076 filed on Jun. 14, 2018, which is incorporated by reference in its entirety.

FIELD OF THE INVENTION

The invention relates to extracellular matrix (ECM) accumulation and more particularly to composition and methods for either increasing or decreasing the same.

BACKGROUND OF THE INVENTION

The skin is the largest organ of the human body and 70% of its dry weight is comprised of extracellular matrix (ECM). The majority of ECM is found within the dermis, primarily composed of type I collagen and protein components such as fibronectin and proteoglycans. Fibroblasts are the predominant mesenchymal cell type and the main effector of ECM homeostasis, mediating its continuous turnover.

Perturbation of ECM homeostasis leads to diseased states. In particular, excess ECM accumulation is a hallmark of fibrotic diseases such as keloid/hypertrophic scaring, scleroderma, and fibrosis induced by medication, surgery, or radiotherapy. The cascade of events that establish fibrosis is complex and remain incompletely understood. It involves multiple mediators acting through an interactive network of signaling pathways to dysregulate ECM homeostasis[1]. Given that metabolism is downstream and necessary for all cellular functions, divergent upstream signaling pathways may converge at key metabolic alterations to ultimately regulate phenotype. In tumor biology, pathways that promote tumor growth merge to induce a reliance on glycolysis, termed the Warburg Effect, which provides anabolic metabolites necessary for proliferation[2]. In inflammation, pro-inflammatory M1 versus anti-inflammatory M2 macrophage polarization is regulated through the balance between glycolysis and fatty acid oxidation (FAO)[3]. Conversely, ECM accumulation might be desired in certain instances, such as wound healing or in regenerative medicine.

SUMMARY OF THE INVENTION

In an aspect, there is provided a method of treating a disease associated with extracellular matrix (ECM) accumulation in a patient, the method comprising administering to the patient a therapeutically effective amount of fibroblasts which express CD36.

In an aspect, there is provided a method of treating a disease associated with extracellular matrix (ECM) accumulation in a patient, the method comprising administering to the patient a therapeutically effective amount of an agent capable of shifting ECM homeostasis from glycolysis to fatty acid oxidation (FAO).

In an aspect, there is provided a method of increasing extracellular matrix (ECM) accumulation in a patient, the method comprising administering to the patient a therapeutic agent capable of shifting ECM homeostasis from fatty acid oxidation (FAO) to glycolysis.

In an aspect, there is provided a use of a therapeutically effective amount of fibroblasts which express CD36 in the preparation of medicament for the treatment of a disease associated with extracellular matrix (ECM) accumulation in a patient.

In an aspect, there is provided a use of a therapeutically effective amount of an agent capable of shifting ECM homeostasis from glycolysis to fatty acid oxidation (FAO) in the preparation of medicament for the treatment of a disease associated with extracellular matrix (ECM) accumulation in a patient.

In an aspect, there is provided a use of a therapeutic agent capable of shifting ECM homeostasis fatty acid oxidation from (FAO) to glycolysis in the preparation of medicament for increasing extracellular matrix (ECM) accumulation in a patient.

In an aspect, there is provided a therapeutically effective amount of fibroblasts which express CD36 for use in the treatment of a disease associated with extracellular matrix (ECM) accumulation in a patient.

In an aspect, there is provided a therapeutically effective amount of an agent capable of shifting ECM homeostasis from glycolysis to fatty acid oxidation (FAO) for use in the treatment of a disease associated with extracellular matrix (ECM) accumulation in a patient.

In an aspect, there is provided a therapeutic agent capable of shifting ECM homeostasis from fatty acid oxidation (FAO) to glycolysis for use in increasing extracellular matrix (ECM) accumulation in a patient.

BRIEF DESCRIPTION OF FIGURES

These and other features of the preferred embodiments of the invention will become more apparent in the following detailed description in which reference is made to the appended drawings wherein.

DETAILED DESCRIPTION

Figure 1:
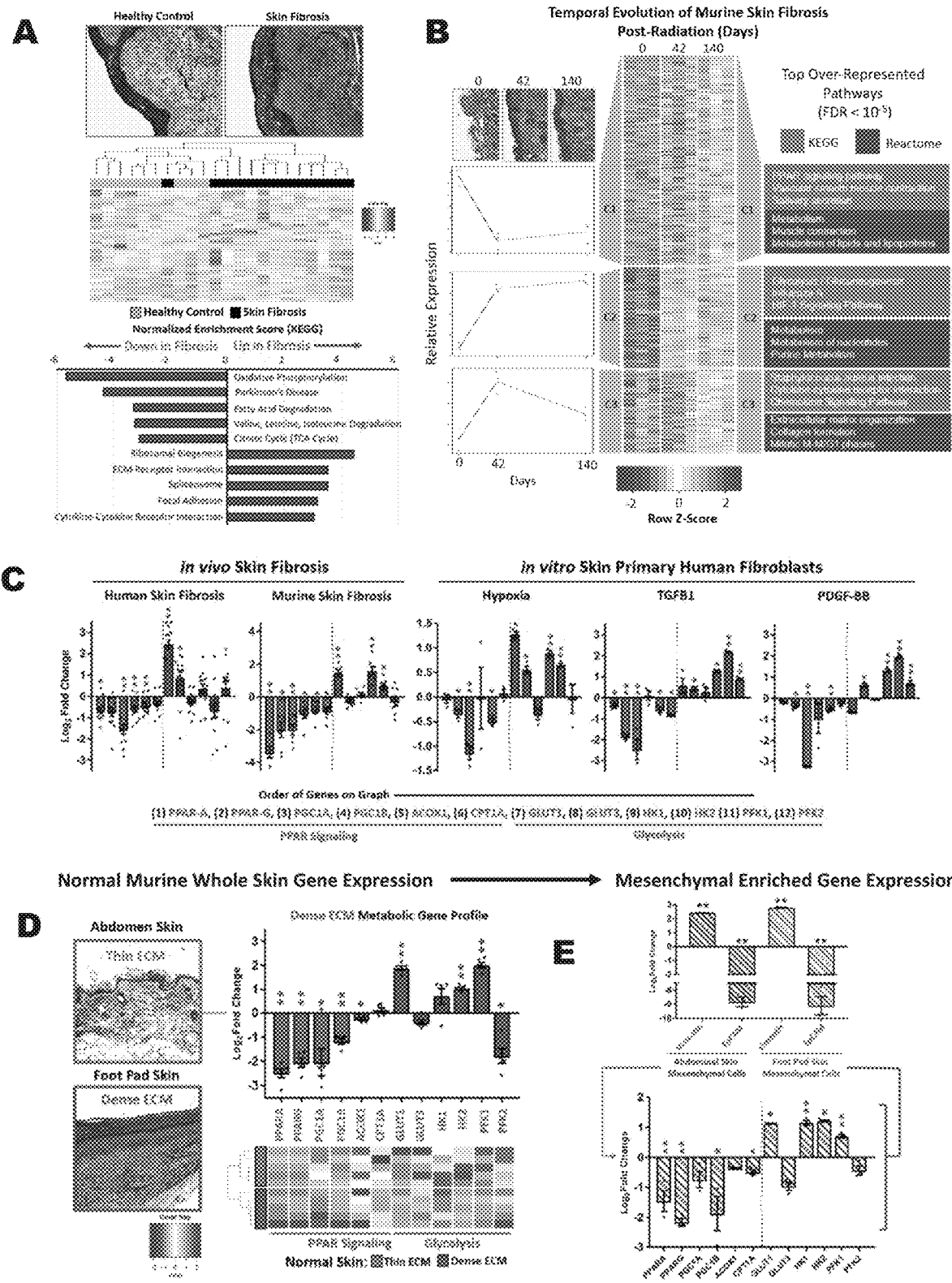
FIG. 1 shows extracellular matrix accumulation (ECM) in normal and fibrotic skin corresponds to a shift in metabolism from fatty acid oxidation to glycolysis. (A) Genome-wide transcriptome (HT-12 array) comparison of normal and fibrotic human skin reveals a shift from catabolism to anabolism. (Top) Trichrome sections of normal and fibrotic skin. (Middle) Unsupervised hierarchical clustering of skin samples based on top 1000 variant genes for healthy and radiation-induced fibrotic skin samples. Fisher's exact test $P=0.00002$ of the two largest clusters. (Bottom) Top pathways (FDR<0.05) altered in skin fibrosis ranked by normalized enrichment scores after KEGG enrichment analysis using all genes for healthy control and skin fibrosis samples. Reactome results are found in FIG. 6. n=9 healthy controls, n=13 skin fibrosis. (B) Temporal analysis of genome wide transcriptomic alterations in murine skin fibrosis demonstrated a shift from PPAR signaling to glycolysis. RNA-seq was performed on 40 Gy irradiated skin tissue at 0, 42, and 140 days post-radiation. Expression patterns were separated into 3 clusters using maSigPro after cluster number optimization using the Silhouette method, which was found to be k=3. (Left) Expression patterns of the three clusters with corresponding trichrome stained skin section above. (Middle) Heatmap of expression pattern for each cluster. (Right) Over-representation pathway analysis using KEGG and Reactome for each pattern displayed on right. n=3 for each time point. (C-E) Pair wise fixed reallocation randomization test performed using REST. (C) A consistent shift from PPAR signaling to glycolysis is seen in skin fibrosis in vivo and in dermal primary human fibroblasts (dPHFs) induced to produce ECM in vitro. qRT-PCR of genes in PPAR signaling and glycolysis relative to untreated control (grey). (Left) In vivo profiling of human and murine skin fibrosis. Human: n=13 skin fibrosis, n=9 control. Murine: n=7 skin fibrosis, n=5 control. (Right) In vitro profiling of dPHFs with hypoxia (2%), TGF-B1 (3 ng/ml), and PGDF-BB (5 ng/ml). n=3 per group. (D) Normal murine skin exhibits PPAR signaling downregulation and glycolysis upregulation with increasing ECM accumulation. (Left) Trichrome staining of thin ECM abdominal skin and dense ECM foot pad skin. (Top-Right) qRT-PCR gene expression of dense ECM skin relative to thin ECM skin (grey). (Bottom-Right) Unsupervised hierarchical clustering using PPAR signaling and glycolysis genes of dense vs. thin ECM murine skin. n=5 per group. (E) Normal murine skin mesenchymal enriched PPAR and glycolysis gene expression. (Top) Abdominal and foot pad skin were dissociated and plated to enrich for vimentin expressing (mesenchymal) cells with no detectable EpCAM expression, as assessed by qRT-PCR. (Bottom) qRT-PCR of PPAR signaling and glycolysis genes. n=3 per group. All data is expressed as mean±s.e.m. *P<0.05, **P<0.01.

In the following description, numerous specific details are set forth to provide a thorough understanding of the invention. However, it is understood that the invention may be practiced without these specific details.

Extracellular matrix (ECM) homeostasis is essential for normal tissue function. Disruption of homeostasis by iatrogenic injury, trauma, or disease results in fibrosis. Skin ECM homeostasis is maintained by a complex process involving an integration of cytokine and environmental mediators. It is unclear, in both normal and disease states, how these multifactorial processes converge to shift ECM homeostasis towards accumulation or degradation. As described herein, an interplay between fatty acid oxidation (FAO) and glycolysis was found to be a key convergence point governing ECM homeostasis in skin. A consistent shift from FAO to glycolysis was observed in human and murine skin with ECM accumulation and in dermal fibroblasts induced to upregulate ECM production by multiple mediators (TGFB1, PDGF-BB, hypoxia). Pharmacologic inhibition and genetic knockdown of key FAO and glycolysis pathway enzymes in dermal fibroblasts confirmed that FAO and glycolysis have antagonistic roles in ECM regulation. Specifically, glycolysis induced an anabolic fibroblast that upregulated ECM production. This was counteracted by shifting fibroblasts to FAO, which induced a catabolic phenotype inhibiting both ECM synthesis and enhancing ECM internalization and lysosomal degradation. CD36, a multifunctional fatty acid transporter, was found to be a critical mediator connecting the metabolic state of fibroblasts with their capacity for ECM regulation. CD36 promoted the catabolic effect of a FAO fibroblast, as its knockdown abrogated the internalization and degradation of collagen-1. Restoring FAO and upregulating CD36, either through pharmacotherapy or by autologous transplantation of $CD36^{high}$ fibroblasts, reduced ECM accumulation in murine radiation-induced skin fibrosis. Our findings indicate that metabolic regulation may be an integration point downstream of molecular signaling pathways and govern ECM homeostasis by shifting fibroblasts between ECM anabolism and catabolism. These results have broad implications for therapies aimed at ECM reduction, such as fibrosis, or ECM buildup, such as regenerative medicine and aging.

In an aspect, there is provided a method of treating a disease associated with extracellular matrix (ECM) accumulation in a patient, the method comprising administering to the patient a therapeutically effective amount of fibroblasts which express CD36.

In an embodiment, the fibroblasts are CD36high.

As used herein, "therapeutically effective amount" refers to an amount effective, at dosages and for a particular period of time necessary, to achieve the desired therapeutic result. A therapeutically effective amount of the pharmacological agent may vary according to factors such as the disease state, age, sex, and weight of the individual, and the ability of the pharmacological agent to elicit a desired response in the individual. A therapeutically effective amount is also one in which any toxic or detrimental effects of the pharmacological agent are outweighed by the therapeutically beneficial effects.

In an aspect, there is provided a method of treating a disease associated with extracellular matrix (ECM) accumulation in a patient, the method comprising administering to the patient a therapeutically effective amount of an agent capable of shifting ECM homeostasis from glycolysis to fatty acid oxidation (FAO).

ECM homeostasis (including the shift of the same from glycolysis to fatty acid oxidation (FAO), and vice versa, and agents for affecting the same) is a mechanism understood by the person skilled in the art (See e.g., Watt, F. M. Mammalian skin cell biology: at the interface between laboratory and clinic. Science 346, 937-40 (2014); Vander Heiden, M. G., Cantley, L. C. & Thompson, C. B. Understanding the Warburg Effect: The Metabolic Requirements of Cell Proliferation. doi:10.1126/science.1160809; and Kelly, B. & O'Neill, L. A. Metabolic reprogramming in macrophages and dendritic cells in innate immunity. Cell Res. 25, 771-784 (2015)).

In an embodiment, the agent capable of shifting ECM homeostasis from glycolysis to fatty acid oxidation (FAO) is sirolimus, mepacrine, benzamil, benzethonium chloride, 0317956-0000, methylergometrine, lovastatin, hydroflumethiazide, maprotiline, mifepristone, tonzonium bromide, clofibrate, fluvastatin, dihydroergocristine, clindamycin, bromocriptine, flavoxate, ajmaline, etacrynic acid, co-dergocrine mesilate, loperamide, rofecoxib, N-acetyl-L-aspartic acid, metitepine, chlortetracycline, arcaine, viomycin, (−)-isoprenaline, piperacetazine, diperodon, oxymetazoline, fursultiamine, finasteride, lactobionic acid, proguanil, levobunolol, sotalol, lithocholic acid, hydrastinine, etoposide, canadine, depudecin, cinchonidine, levocabastine, haloperidol, amiloride, proxymetacaine, harpagoside, clozapine, diflorasone, arachidonic acid, hemicholinium, fipexide, Prestwick-1080, 10-ethoxyharmalan, sulmazole, azlocillin, amprolium, metixene, alprenolol, altretamine, hydroxyzine, ethosuximide, heliotrine, bromperidol, atracurium besilate, S-propranolol, 0198306-0000, Chicago Sky Blue 6B, pseudopelletierine, butamben, anabasine, ampyrone, homosalate, triflusal, xylometazoline, naphazoline, iopanoic acid, Prestwick-1083, letrozole, isocarboxazid, vigabatrin, epirizole, quinethazone, iocetamic acid, hydrochlorothiazide, naproxen, ramifenazone, chlormezanone, atractyloside, caffeic acid, cefaclor, cinchonine. Preferably, the agent is hydroflumethiazide, N-acetyl-L-aspartic acid, clindamycin, vigabatrin, iocetamic acid, caffeic acid, ethosuximide, iopanoic acid, cefaclor, sotalol, ramifenazone, hydrochlorothiazide, clofibrate, fursultiamine, epirizole, chlormezanone, naproxen, (−)-isoprenaline, triflusal, finasteride, co-dergocrine mesilate, ampyrone, altretamine, heliotrine, cinchonidine, chlortetracycline, sulmazole, etacrynic acid, bromperidol, cinchonine, atractyloside, maprotiline, isocarboxazid, S-propranolol, and canadine.

In some embodiments, the disease is fibrosis, preferably skin fibrosis (keloid scarring, scleroderma, surgical/trauma skin fibrosis), radiation fibrosis (skin, lung, GI), hepatic fibrosis (hepatitis C induced, NASH), renal fibrosis (HTN, diabetes, FSGS), and pulmonary fibrosis (idiopathic pulmonary fibrosis, granulomatous fibrosis, iatrogenic pulmonary fibrosis.

In an aspect, there is provided a method of increasing extracellular matrix (ECM) accumulation in a patient, the method comprising administering to the patient a therapeutic agent capable of shifting ECM homeostasis from fatty acid oxidation (FAO) to glycolysis.

In some embodiments, the agent is PF-01378883-00, PF-00875133-00, pregnenolone, dienestrol, STOCK1N-35215, ioxaglic acid, chrysin, estropipate, citiolone, 16-phenyltetranorprostaglandin E2, natamycin, adipiodone, cyproterone, moxisylyte, nystatin, zidovudine, hexylcaine, dropropizine, bromopride, ranitidine, eldeline, piracetam, pyrantel, mephenytoin, ginkgolide A, ciclopirox, clomipramine, bupivacaine, pyrithyldione, etynodiol, isradipine, roxarsone, isometheptene, pheniramine, and betaxolol.

In some embodiments, the method is for enhancing wound closure, or organ scaffolding for regenerative medicine.

In an aspect, there is provided a use of a therapeutically effective amount of fibroblasts which express CD36 in the preparation of medicament for the treatment of a disease associated with extracellular matrix (ECM) accumulation in a patient.

In an aspect, there is provided a use of a therapeutically effective amount of an agent capable of shifting ECM homeostasis from glycolysis to fatty acid oxidation (FAO) in the preparation of medicament for the treatment of a disease associated with extracellular matrix (ECM) accumulation in a patient.

In an aspect, there is provided a use of a therapeutic agent capable of shifting ECM homeostasis fatty acid oxidation from (FAO) to glycolysis in the preparation of medicament for increasing extracellular matrix (ECM) accumulation in a patient.

In an aspect, there is provided a therapeutically effective amount of fibroblasts which express CD36 for use in the treatment of a disease associated with extracellular matrix (ECM) accumulation in a patient.

In an aspect, there is provided a therapeutically effective amount of an agent capable of shifting ECM homeostasis from glycolysis to fatty acid oxidation (FAO) for use in the treatment of a disease associated with extracellular matrix (ECM) accumulation in a patient.

In an aspect, there is provided a therapeutic agent capable of shifting ECM homeostasis from fatty acid oxidation (FAO) to glycolysis for use in increasing extracellular matrix (ECM) accumulation in a patient.

As used herein, "pharmaceutically acceptable carrier" means any and all solvents, dispersion media, coatings, antibacterial and antifungal agents, isotonic and absorption delaying agents, and the like that are physiologically compatible. Examples of pharmaceutically acceptable carriers include one or more of water, saline, phosphate buffered saline, dextrose, glycerol, ethanol and the like, as well as combinations thereof. In many cases, it will be preferable to include isotonic agents, for example, sugars, polyalcohols such as mannitol, sorbitol, or sodium chloride in the composition. Pharmaceutically acceptable carriers may further comprise minor amounts of auxiliary substances such as wetting or emulsifying agents, preservatives or buffers, which enhance the shelf life or effectiveness of the pharmacological agent.

The advantages of the present invention are further illustrated by the following examples. The examples and their particular details set forth herein are presented for illustration only and should not be construed as a limitation on the claims of the present invention.

EXAMPLES

Methods and Materials

Human Sample Collection and Processing

This study was approved by the research ethics board at University Health Network (REB 15-9359-CE) and informed consent was obtained for each patient. Patients greater than 18 years of age planning to undergo head and neck surgical procedures at the University Health Network between February 2015 to July 2016 were screened for previous radiotherapy. Irradiated patients were included if they received full dose radiotherapy to the neck (50-70 Gy) for cancer therapy, were at least 150 days from completion of treatment, and had a history and physical examination consistent with fibrosis. Patients treated with anti-fibrotic agents and those with fibrotic disorders were excluded. Normal age matched control patients who were also undergoing head and neck surgical procedures were consented. Convenience sampling strategy was utilized. Full thickness dermis from the irradiated or normal neck was taken on the day of surgery and suspended in PBS. Samples were divided for transcriptome and metabolite profiling and then snap frozen in liquid nitrogen for storage.

Human RNA Transcriptome Processing

Human dermal tissue was pulverized using liquid nitrogen mortar and pestle. RNA was extracted using Qiagen RNeasy. RNA that passed quality threshold using Agilent 2100 Bioanalyzer (RIN>7) were then run on the Human HT-12 V4 BeadChips (Illumina) according to manufacturer's instructions. Data was checked for overall quality using the LUMI Bioconductor package in R (v2.15.3). Data was normalized using quantile normalization followed by a per probe median centered normalization. Probes which were above the $20^{th}$ percentile of the distribution of intensities in 80% of one of the two groups were included for analysis.

Animal Experiments

All animal procedures were approved by Animal Care Committee at the University Health Network under AUP 3422. A murine skin fibrosis model was created by radiating the hindlimb of C3H/HeJ mice (Jackson Laboratory) or B6.12951-Cd36$^{tm1Mfe}$/J mice (Jackson Laboratory) using an XRAD 225Cx (Precision X-Ray) and a 2.5 cm collimator. Prior to irradiation, fluoroscopic imaging was used to confirm and standardize the irradiation site. 40 Gy for C3H mice or 30 Gy for B6 mice was divided equally on the dorsal and ventral side of the leg. Animals were randomized into groups for treatment by a researcher blinded to treatment assignment. For CD36$^{high}$ cell treatment, 1×10$^6$ cells in 100 ul PBS were injected into the hindlimb subdermally at 3 sites weekly for 3 weeks starting at 4 weeks post-irradiation. For caffeic acid phenethyl ester treatment, 10 mg/kg was given by intraperitoneal injection by a researcher blinded to treatment. Caffeic acid phenethyl ester or vehicle control was given 3× per week for 10 weeks starting at 1 week post-irradiation. Leg contracture measurement was performed, as previously published[21], after first sedating mice with inhalation anesthesia and ensuring deep sedation through no pain reflex and no muscle tone. Then mice hips were fixed on a custom apparatus. 0.1N equivalent weight was then used to extend the fibrotic and contralateral normal leg and leg extension was measured using a standardized ruler by two assessors blinded to treatment groups. Percentage leg contracture was calculated as 1–leg extension of fibrotic leg/leg extension of contralateral normal leg. Leg contracture was measured biweekly and averaged for the week.

Murine RNA-Seq Processing

For temporal transcriptome profiling, normal and/or fibrotic skin tissue was dissected at 0, 36, and 140 days post-radiation from age matched C3H/HeJ mice. CD36$^{high}$ cells were collected at 16 weeks post-treatment along with vehicle controls. CD36$^{high}$ vehicle control was also used as the last time point for temporal transcriptome profiling. Samples were snap frozen in liquid nitrogen. For RNA extraction, samples were liquid nitrogen pulverized using mortar and pestle. RNeasy (Qiagen) was used for RNA extraction as per manufacturer's instructions. RNA samples were quantified using the qubit RNA kit (Life Technologies) on the Qubit 2.0 fluorometer. The RNA integrity was assessed using the Agilent RNA 6000 nano chip on the Agilent Bioanalyzer 2100. Each sample had a RIN score greater than 8.0 and 250 ng of each sample was used for library prep. Libraries were prepared using the TruSeq Stranded mRNA library prep kit with no deviation from manufacturer's instructions (Illumina). Final cDNA libraries were size validated using the Agilent Bioanalyzer 2100 and quantified by qPCR (Kapa Biosystems). All libraries were normalized to 10 nM, pooled 5 samples per pool, and diluted down to 2 nM. 2 nM pools were denatured using 0.2N NaOH and diluted to a final concentration of 10 pM. 10 pM pools were loaded onto the Illumina cBot for cluster generation. The clustered flow cell was sequenced paired-end 100 cycles using v3 reagents on the Illumina HighSeq 2000 at the Princess Margaret Genomics Facility to achieve a minimum of 30 million reads per sample. Raw RNA-seq data quality control was performed using FASTQC v.0.11.2 (Babraham Bioinformatics). Quality metric assessed for each sample include per-base sequence quality, per-tile sequence quality, per-base sequence content, per-sequence GC content, sequence length distribution, duplication levels, over-represented sequences and adapter content. All samples were considered acceptable based on FASTQC analysis. Tophat and Cufflinks were used as previously described[22]. Raw sequencing data was aligned to human genome using Bowtie (version 2.2.3) and Tophat (version 2.0.13). Transcript assembly was performed using Cufflinks (version 2.2.1). Post-alignment QC was performed using RNA-SeQC (version 1.1.7). Read count metrics, such as total, unique, duplicate reads, mapped reads, mapped unique reads, transcript annotated reads, and expressed transcripts and coverage metrics, including mean coverage, mean coefficient of variation, coverage gaps, 5/3' coverage, GC bias, coverage plots, and cumulative gap length were assessed for each sample. All samples passed post-alignment QC.

Untargeted Metabolomics Processing

Fibrotic and normal murine skin samples were pulverized in liquid nitrogen using a custom mortar and pestle. For metabolite extraction, samples were resuspended in PBS at 100 mg/ml. 50 ul was used for metabolite extraction. $^{13}C_6$-phenylalanine (2 μl at 250 ng/μl) was added as internal standard (IS) to all samples. Mass Spectrometer (Agilent Technologies 6550 Q-TOF) coupled with an Ultra High Pressure Liquid Chromatograph (1290 Infinity UHPLC Agilent Technologies) was used. Profiling data was acquired under both positive and negative electrospray ionization conditions over a mass range m/z of 100-1700 at a resolution of 10,000 (separate runs) in scan mode. Metabolite separation was achieved using two columns of differing polarity, a hydrophilic interaction column (HILIC, ethylene-bridged hybrid 2.1×150 mm, 1.7 mm; Waters) and a reversed-phase C18 column (high-strength silica 2.1×150 mm, 1.8 mm; Waters) with gradient described previously[23]. Samples were injected in duplicate, wherever necessary, and a pooled quality control (QC) sample, made up of all of the samples from each study was injected several times during a run. A separate plasma quality control (QC) sample was analyzed with pooled QC to account for analytical and instrumental variability. Auto-MS/MS data was also acquired with pooled QC sample to aid in unknown compound identification using fragmentation pattern. Data alignment and filtering was performed using Mass Profiler Professional (Agilent). Default settings were used with the exception of signal-to-noise ratio threshold (3), mass limit (0.0025 units), and time limit (9 s). Putative identification of each metabolite was done based on accurate mass (m/z) against METLIN database using a detection window of ≤7 ppm. Metabolites detected in at least ≥80% of one of two groups were selected for differential expression analyses.

Cell Culture dPHFs obtained from ATCC (PCS-201-012) were cultured in DMEM with 5% FBS. Mesenchymal cells were isolated primarily from C3H or B6 mice. Animals were euthanized and intraperitoneal fat or skin was dissected and minced. Collagenase and hyaluronidase (Stem cell technologies) digestion was performed in a rotating oven at 37 C for 1 hour, passed through a 70 uM filter, and then plated in DMEM+10% FSB to expand the mesenchymal population. Cells were starved for 12 hours in MEM media prior to treatment with TGF-B1 (Sigma), caffeic acid (Sigma), dichloroacetic acid (Sigma), PDGF-BB (R&D Systems), and/or etomoxir (Tocris). All protein and mRNA profiling was performed at 24 hours post-treatment except for PDGF-BB, which was performed at 48 hours post-treatment.

ELISA Screening for Drug Compounds

Human fibroblasts were seeded onto 96-well plates (2000 cells/well). One day later, the cells were treated with TGFβ1 (10 ng/mL) and compounds as indicated. Seventy-two hours later, supernatant was collected and assayed for pro-Collagen1a1 secretion (Human Pro-Collagen I alpha I ELISA Kit, Abcam; ab210966)

Trichrome Quantification

Formalin-fixed, paraffin-embedded 8 um sections treated with Masson's Trichrome Stain were whole slide scanned using Aperio ScanScope XT. Analysis was performed by a researched blinded to treatment. Using ImageJ, whole slide scanned images were loaded using the Bioanalyzer plugin, and then stacked to RGB. Colour deconvolution was used to separate the full-colour images into their red, green and blue components. A threshold of pixel intensity was optimized and set and standardized for all images. A ratio of blue (trichrome) to red (nuclear) pixel density was derived for each image, representing collagen to cell ratio.

Western Blot

For supernatant proteins, supernatant was spun down at 6000 g×10 minutes at 4° C. For cell lysate, protein was extracted in RIPA buffer with a protease inhibitor (Roche) and spun down at 6000 g×10 minutes at 4 C. Antibodies used: Collagen-1 (ab138492, abcam, 1:5000), Fibronectin (ab2413, abcam, 1:5000), PAI-1 (sc5297, Santa Cruz, 1:1000), beta-actin (ab8229, abcam, 1:1000).

qRT-PCR

For human and murine skin samples, skin samples were macrodissected and snap frozen in liquid nitrogen and stored at −80° C. For in vitro experiments, cells were trypsinized and either snap frozen in liquid nitrogen or immediately underwent RNA extraction. All RNA was extracted using the RNeasy Mini Kit (Qiagen) according to manufacturer instructions. RNA quality was measured and quantified using either the NanoDrop 2000c Spectrophotometer (Thermo Scientific); we used either A260/280 for cell samples, or RIN for human and murine samples using a 2100 bioanalyzer (Aligent). cDNA was synthesized from normalized amounts of RNA using random hexamer primers and SuperScript III (Invitrogen) on a PTC-200 Peltier Thermal Cycler. Primers were obtained from peer-reviewed publications whenever possible. See Table S1 for references and amplicon size. Primers were validated through BLASTing to ensure specificity, size confirmation by gel electrophoresis at first time use, and by melting curve assessment for all reactions. PCR efficiency was measured using a standard curve through the dilution of a representative sample to determine the linear range of cDNA amounts for qRT-PCR reactions. qRT-PCR reactions were performed on 384-well plates (Applied Biosystems) using SYBR Green PCR Master Mix (Applied Biosystems). The analysis was run on the 7900HT Fast Real-Time PCR System (Applied Biosystems). Reaction conditions for cDNA synthesis and qRT-PCR are found in supplementary data Table S2 and S3 respectively. A no template control was used to monitor contamination and false positive results from primer-dimers. Results of no template controls were confirmed to have higher CT-values and distinct melting curves compared to template reactions. 18S ribosomal RNA was used as an internal control. A $2^{-\Delta\Delta CT}$ method was used for relative quantification and for graphical representation in figures. Statistical analysis was performed on biological replicates using Relative Expression Software Tool (REST)[24] set to default parameters.

Flow Cytometry

For DQ-collagen-1 and CD36 experiments, dPHFs were treated as per above (cell culture) for 24 hours. DQ-collagen-1 (Sigma) at 4 ug/ml was added and incubated with cells for an additional 5 hours. Cells were then prepared for flow cytometry using 5 ul of CD36-PE (336206, Biolegend) added to 200,000 cells in 100 ul FACS buffer (PBS+1% FBS) and incubated for 30 minutes on ice. DAPI (1:2000) was added just prior to flow cytometry for identification of live cells. For cell surface profiling, cells were incubated in separate FACS tubes with CD31-PECy7 (102418, BioLegend) and CD45-PECy7 (102418, BioLegend).

CRISPR-Cas9 Knockdown

Guide RNAs were created using web tool (http://crispr.mit.edu/). CD36 Guide 1: CGGAACTGTGGGCT-CATCGC, CD36 Guide 2: TGGGCTGTGACCG-GAACTGT, PPARG Guide: CTCCGTGGATCTCTCCGTAA, ACOX-1 Guide: TGACAGCCACCTCATAACGC, HK2 Guide: TGACCA-CATTGCCGAATGCC. pSpCas9(BB)-2A-GFP (Addgene, 48138) was used. Protocol was performed as previously described[25]. 5×10$^5$ dPHFs were electroporated with 5 ug of construct using an Amaxa mouse neural stem cell nucleofactor kit (Lonza). Cells were grown for 24 hours and then sorted for GFP.

SMAD3 Luciferase Reporter

SMAD3 luciferase reporter was constructed as previously described[26]. Oligos containing SMAD3 binding sites were designed with BamH1 and Sal1 digestion sites. Forward: 5'-GATCCGAGCCAGACAAAAAGCCAGACATT-TAGCCAGACACG-3', reverse: 5'-TCGACGTGTCTGGCTAAATGTCTGGCTTTTTGTC TGGCTCG-3'. SMAD oligoes were inserted into a p-delta-51 LUC II reporter. dPHFs were electroporated with construct using an Amaxa mouse neural stem cell nucleofactor kit (Lonza). 24 hours after electroporation, cells were treated as above (cell culture) for 24 hours and lysed to assess for luciferase and renilla activity. Relative luciferase activity was defined as the level of luciferase bioluminescence divided by renilla bioluminescence for each sample.

GFP CD36$^{high}$ Cell Localization pHAGE PGK-GFP-IRES-LUC-W packaged lentivirus was created by transient transfection of 293T cells and infected into CD36$^{high}$ fibroblasts. CD36$^{high}$ fibroblasts were sorted for GFP positivity and injected into murine skin fibrosis. For localization of GFP-CD36$^{high}$ fibroblasts, skin fibrosis tissue was dissected 7 days post-transplantation and 8 um FFPE sections were created. Adjacent FFPE sections were stained with hematoxylin and eosin (H&E) or anti-GFP (ab6556, Abcam, 1:1000), secondary Cy3 (ab6939, Abcam, 1:2000), and DAPI. H&E sections were imaged using Leica DC300 and immunofluorescence was imaged with an Olympus Fluoview laser-scanning confocal microscope.

Lysosome Quantification dPHFs were treated as per above (cell culture) and exposed to LysoTracker (ThermoFisher) as per manufacturer's instructions on a 4 chamber cover glass system (ThermoFisher). Images were obtained using an Olympus Fluoview laser-scanning confocal microscope. Fluorescence intensity was quantitated per cell using the Object Identification module and Measurement function of Volocity software. Cell area was measured using ImageJ software.

Live Cell Imaging and Quantification dPHFs were treated as per above (cell culture) on an 8 chamber cover glass system (ThermoFisher) for 24 hours prior to addition of DQ-collagen-1 (4 ug/ml) (ThermoFisher) or FITC-collagen-1 (7 ug/ml) (chondrex). Cells were assessed immediately by live cell imaging using a Quorum WaveFX spinning disk confocal system. 3-5 locations per well were selected at random for imaging every 6 minutes at 20× magnification. Fluorescence intensity was quantitated using the object identification and measurement modules in Volocity. Overall fluorescence intensity was measured as the sum of all identified objects within the selected threshold. Cell area was measured using ImageJ software.

FAO and Glycolysis Functional Assessment for dPHFs

Seahorse experiments were performed on an XFe96 analyzer (Aligent) based on manufacturer's instructions. dPHFs were prepared as per above (cell culture) on an XF96 culture plate. For glycolysis profiling, final concentration of glucose (1 mM or 10 mM), oligomycin (1 uM), and 2-DG (100 mM) was utilized. For FAO, palmitate sodium (Sigma) and BSA-fatty acid free (Sigma) were used to make palmitate-BSA (0.17 mM) as per manufacturer's instructions. Etomoxir (Tocris) 40 uM final concentration was used.

Statistical Analysis

Transcriptomic data can be found on NCBI GEO using ID: GSE98157 for murine RNA-seq data and GSE98159 for human HT-12 array data. Software parameters have been uploaded onto Github: https://github.com/bhklab/SkinFibrosis.

Differential expression for murine RNA-seq: Cufflinks (version 2.2.1) was used for murine RNA-seq statistical testing with no deviation from the standard pipeline as originally described by Trapnell et al.[22]. Files were then loaded into CummeRBund for final output of significance testing, results, and graphing.

Differential expression for human transcriptome and metabolomic datasets: A moderated Student t-test with Benjamini-Hochberg false discovery rate (FDR) correction for multiple testing was performed on $log_2$-transformed gene expression or metabolite levels for differential expression.

Pathway enrichment analysis: Two methods were used for enrichment analyses using KEGG and Reactome. 1—GSEA was performed using the Broad Institute GSEA software. 2—Over-representation. Piano R package (version 1.8.2) was utilized to perform hypergeometric testing on genes which were FC>1.25 and FDR<0.05.

Computational Pharmacogenomics: The Connectivity Map (CMAP) dataset was normalized using Robust Multi-array Average (RMA) as performed in our PharmacoGx package (version 1.1.6)[7,27,28]. Each gene was fitted using a linear model adjusted for batches and cell line and ranked the genes with respect to their associated Student t statistics in order to build a "perturbation signature" for each compound tested in CMAP. Differentially expressed genes between human fibrotic and normal skin were ranked based on their associated t statistics, referred to as "query signature". A second query signature was created using the curated genes in KEGG for PPAR Signaling and glycolysis. These two query signatures were used to query CMAP and accordingly two ranked lists of drugs were obtained. Drugs were ranked according to their connectivity score in descending order. The overlap between the high ranked drugs (positive connectivity score) of the two lists were obtained and ranked based on their lethal dose 50 (LD50).

Human Hierarchical clustering and heatmap: For each gene, a probe was selected with the maximum interquartile range. The mapped genes were ranked according to the variance of their expression across the entire data. The top most variant genes were selected and used for hierarchical clustering (correlation distance and complete linkage) and generating a heatmap (gplots_3.0.1). Finally, to measure significance of the clustering results, a fisher test was performed on the two largest clusters and compared with the true labels of the samples.

Temporal clustering: MaSigPro R package (version 1.40.0), updated for clustering temporal RNA-seq data, was used. Genes which were significantly expressed (FDR<0.05) between time points 0 and 42 days and between 42 and 140 days were aggregated. MaSigPro (v. 1.40.0) pipeline was utilized for hierarchical cluster and visualization of clusters. Optimal number of clusters were defined by the silhouette method originally described by Rousseeuw et al. 1987[29]. The most parsimonious solution of k=3 was selected.

Results and Discussion

Figure 5:
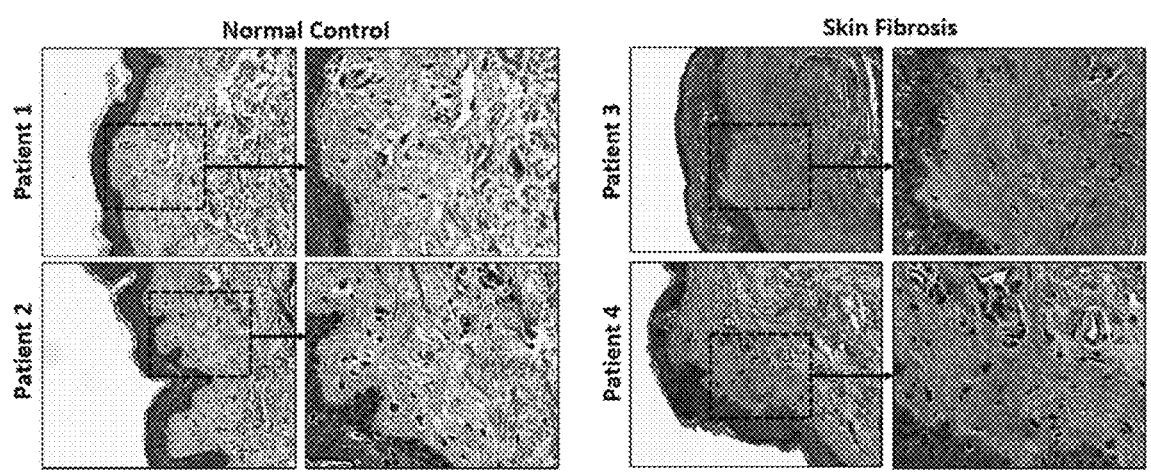
FIG. 5 shows extracellular matrix deposition in the skin of patients post-radiotherapy. Trichrome stained skin sections. (Left) Neck skin tissue from healthy controls. (Right) Neck skin tissue from patients treated with 70 Gy for head and neck cancer.
Figure 6:
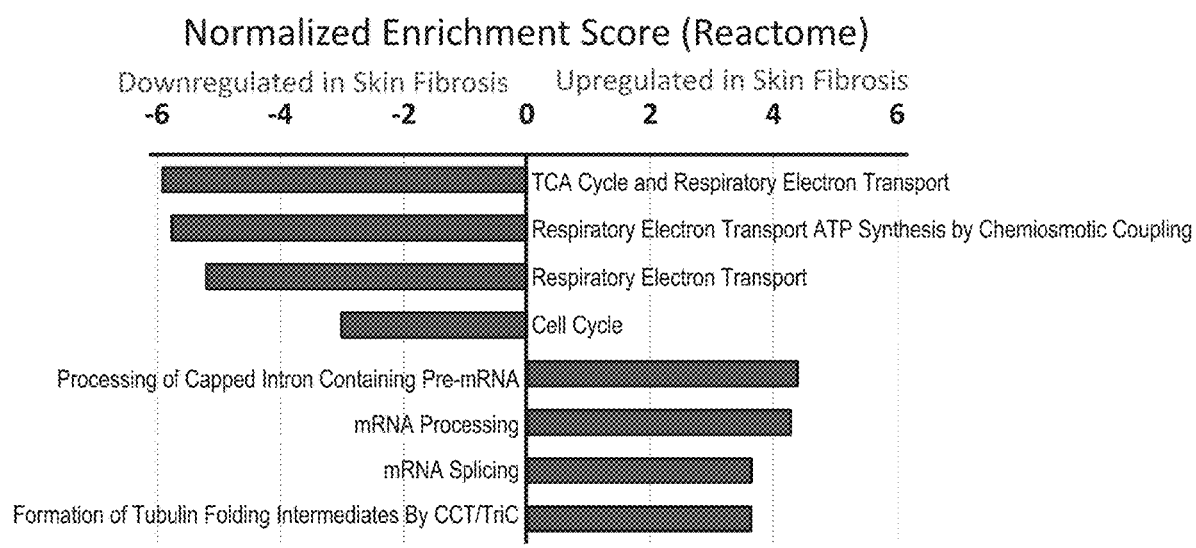
FIG. 6 shows pathways altered in human radiation-induced skin fibrosis assessed by REACTOME gene set enrichment analysis. Top pathways altered by radiation based on normalized enrichment score. Scores are relative to healthy control. FDR<0.05 for all pathways. n=13 skin fibrosis, n=9 normal. Parkinson's disease was ranked 3$^{rd}$ in downregulated pathways and was removed for clarity given that it is not a biological pathway.

To uncover metabolic alterations which drive ECM regulation, genome-wide transcriptome profiling was performed on human skin fibrosis post-radiotherapy and on age-matched healthy controls. Indeed, skin fibrosis is a common long term sequala for cancer patients treated with radiotherapy[4]. Hierarchical clustering of gene expression profiles revealed a significant separation between the two groups (FIG. 1A, FIG. 5). Pathway analysis via gene set enrichment analysis (GSEA) showed that the most significantly downregulated genes in fibrosis were in catabolic pathways involved in oxidative phosphorylation, FAO, and the tricarboxylic acid (TCA) cycle (FIG. 1A, FIG. 6). These pathways are linked, as fatty acids undergoing oxidation are ultimately catabolized in the TCA cycle through oxidative phosphorylation in the mitochondria. Conversely, top upregulated pathways in fibrosis were associated with anabolism, such as ribosome biogenesis, spliceosome function, and mRNA processing (FIG. 1A, FIG. 6).

Figure 7:
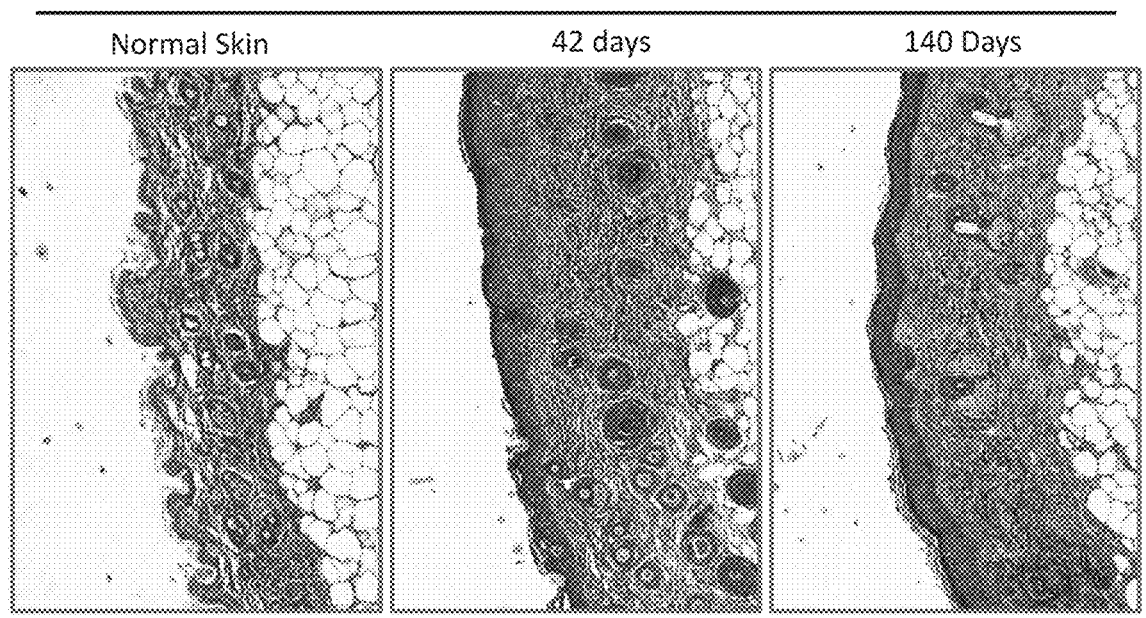
FIG. 7 shows temporal accumulation of extracellular matrix deposition in murine skin post-radiotherapy. Trichrome stained skin sections of murine C3H hindlimb skin obtained at 0, 42, and 140 days post-radiotherapy.

To further characterize metabolic dysregulation in skin fibrosis and elucidate its temporal evolution, genome-wide transcriptome profiling was performed on a murine model of radiation-induced skin fibrosis at 0, 42, and 140 days post-radiation (FIG. 1B, FIG. 7). Hierarchical clustering was performed on temporal expression patterns. Pathway analysis of the largest clusters revealed an early and sustained increase in glycolysis after radiation and a reciprocal decrease in PPAR (peroxisome proliferator-activated receptor) signaling (FIG. 1B). PPAR signaling activates pathways involved in FAO and mitochondrial oxidative metabolism. Its downregulation inhibits fatty acid degradation, the TCA cycle, and oxidative phosphorylation; potentially accounting for the similar pattern of catabolic downregulation observed in human skin fibrosis.

qRT-PCR confirmed the downregulation of PPAR signaling in human and murine skin fibrosis through profiling of transcription factors (PPAR-A and PPAR-G), their co-activators (PGC1A, PGC1B) and downstream targets acyl-CoA oxidase 1 (ACOX1) and carnitine palmitoyltransferase 1A (CPT1A), which catalyze rate limiting steps of FAO (FIG. 1C). Conversely, activation of glycolysis was observed at multiple steps of the pathway, including upregulation of glucose transporters (GLUT1/3), hexokinase 1/2 (HK1/2), and phosphofructokinase members (PFK1, PFK2).

Figure 8:
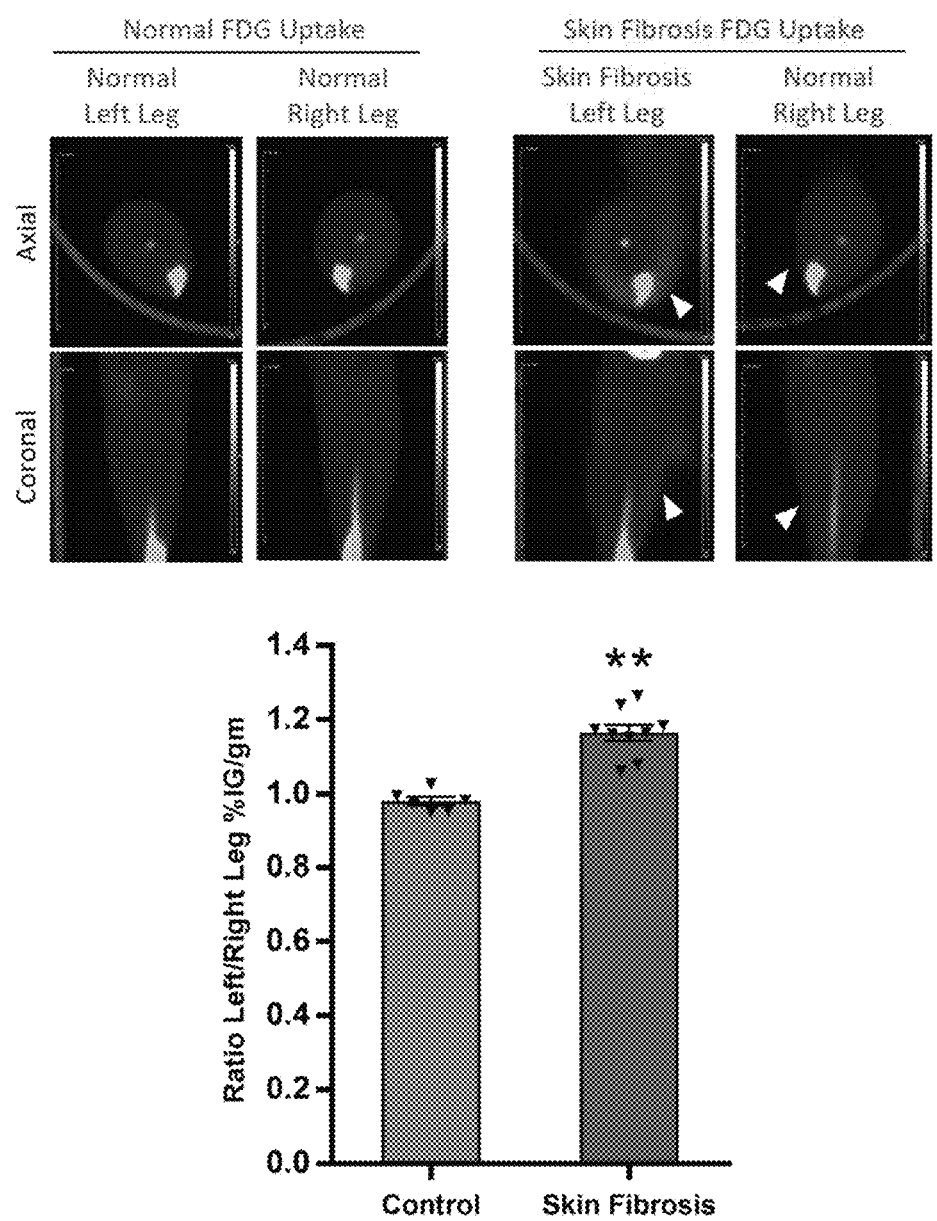
FIG. 8 shows skin fibrosis demonstrates an increase in glucose uptake. PET-CT scans were performed to assess fludeoxygluose (FDG) uptake in normal mice and mice with hindlimb skin fibrosis. (A) Axial and coronal view of FDG uptake from the left and right hind limb in normal mice (left) and mice with skin fibrosis (right). (B) Quantification of ratio of left/right FDG percent injected dose per gram of tissue (% ID/Gm). n=6 control, n=8 skin fibrosis. **P<0.01. Students T-Test.
Figure 9:
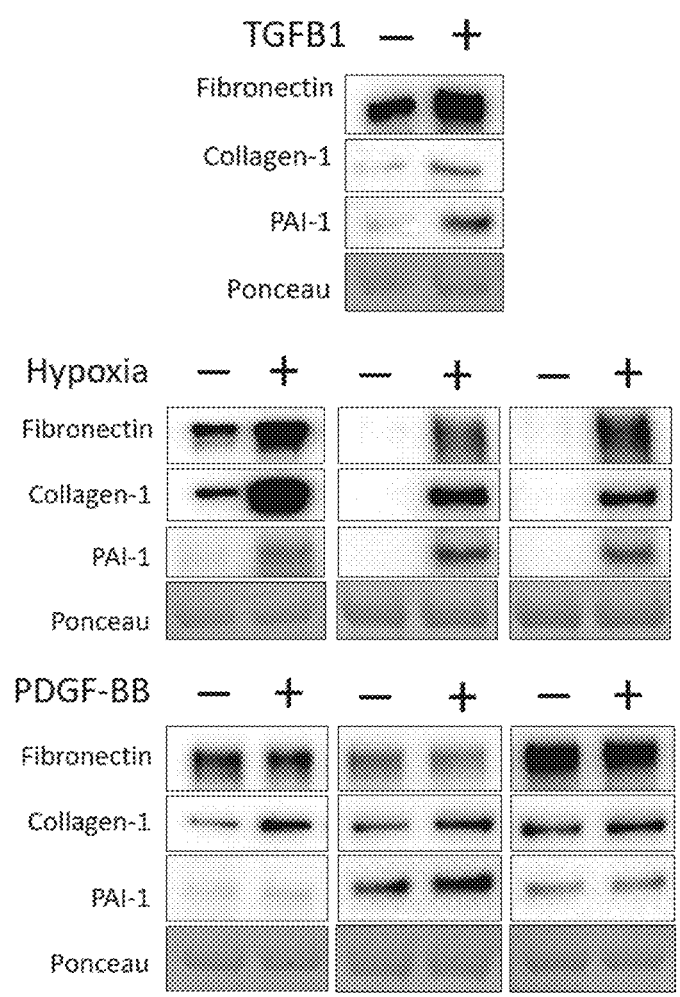
FIG. 9 shows extracellular western blot for fibronectin, collagen-1 and plasminogen activator inhibitor-1 (PAI-1). Relative hypoxia (2% vs. 20% O2), TGF-B1 (3 ng/ml), and PDGF-BB (5 ng/ml) were used to treated dermal primary human fibroblasts. Supernatant was collected at 24 hours post-treatment for TGF-B1, and 48 hours for hypoxia and PDGF-BB. Replicates for TGFB1 treatment are found in main figures (FIGS. 2D, 2E, 2J, 2K).

In vitro studies further demonstrated that multiple mediators known to upregulate ECM production converged on PPAR signaling and glycolysis expression. Dermal primary human fibroblasts (dPHFs) were exposed to hypoxia, TGF-B1, or PDGF-BB, purported to increase ECM production via HIF-1a, SMAD, and MEK/ERK signaling, respectively[5,6]. All three mediators increased the expression of pro-fibrotic proteins: collagen-1, fibronectin, and/or plasminogen activator inhibitor-1 (PAI-1), an inhibitor of fibrinolysis (FIG. 8). All three mediators also downregulated genes in PPAR signaling and upregulated genes in glycolysis, a pattern consistent with human and murine skin fibrosis (FIG. 1C). These transcriptional changes correlated with a functional shift in metabolism from FAO to glycolysis. TGF-B1 treated dPHFs increased glycolysis at baseline and with glucose (FIG. 9A). TGF-B1 also lowered oxygen consumption rate with the addition of the fatty acid palmitate, and was less sensitive to etomoxir, a CPT1A inhibitor, indicating a lower level of FAO (FIG. 9B).

Figure 10:
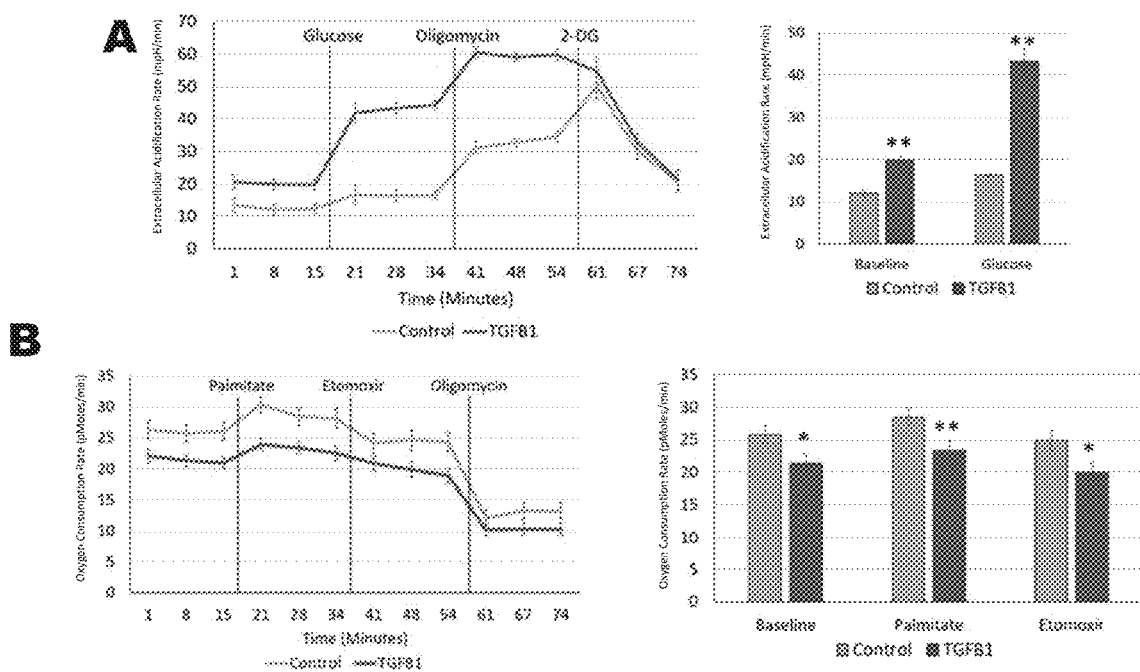
FIG. 10 shows TGF-B1 induced a functional shift from fatty acid oxidation to glycolysis in dermal primary human fibroblasts (dPHFs). dPHFs were treated with 3 ng/ml TGF-B1. (A) Glycolysis stress test. Y-axis plots the extracellular acidification rate which is a measure of glycolysis via the production of lactic acid. Glucose (10 mM), oligomycin (1 uM), and 2-DG (2-Deoxy-Glucose, 100 mM). Oligomycin inhibits ATP synthase which induces maximal glycolysis. 2-DG is a competitive inhibitor of hexokinase and inhibits glycolysis. n=8 per group. (B) Fatty acid oxidation. Y-axis represents oxygen consumption rate, a measure of metabolite oxidation over time. Palmitate (170 uM), etomoxir (40 uM) and oligomycin (2 uM). Etomoxir inhibits FAO by irreversibly binding to CPT-1A, which catalyzed the transport of fatty acids, such as palmitate, into the mitochondria for beta-oxidation. Replicates were normalized by CyQUANT Direct Cell Proliferation Assay Kit. n=15 per group. Student's T-Test. All data is expressed as mean±s.e.m. *P<0.05, **P<0.01.

Furthermore, we asked whether shifts in FAO and glycolysis may be observed in normal skin with variations in ECM accumulation. Murine skin obtained from the foot pad, which has thick and dense ECM, when compared with thin ECM from abdominal skin, displayed a similar downregulation of PPAR signaling and increased glycolysis expression, almost completely mirroring skin fibrosis (FIG. 1D top). Hierarchical clustering using these 12 metabolic genes revealed a clear segregation between skin types (FIG. 1D bottom). Similarly, hierarchical clustering using these metabolic genes segregated normal human skin with thin ECM from dense ECM (FIG. 10). To confirm that this metabolic signature corresponding to ECM accumulation was observed in fibroblasts, mesenchymal cells isolated from murine foot pad displayed a downregulation of PPAR genes and an increase in glycolysis compared to abdominal skin mesenchymal cells (FIG. 1E). Therefore, even in normal states, there is a consistent shift from FAO to glycolysis with ECM accumulation.

Figure 2:
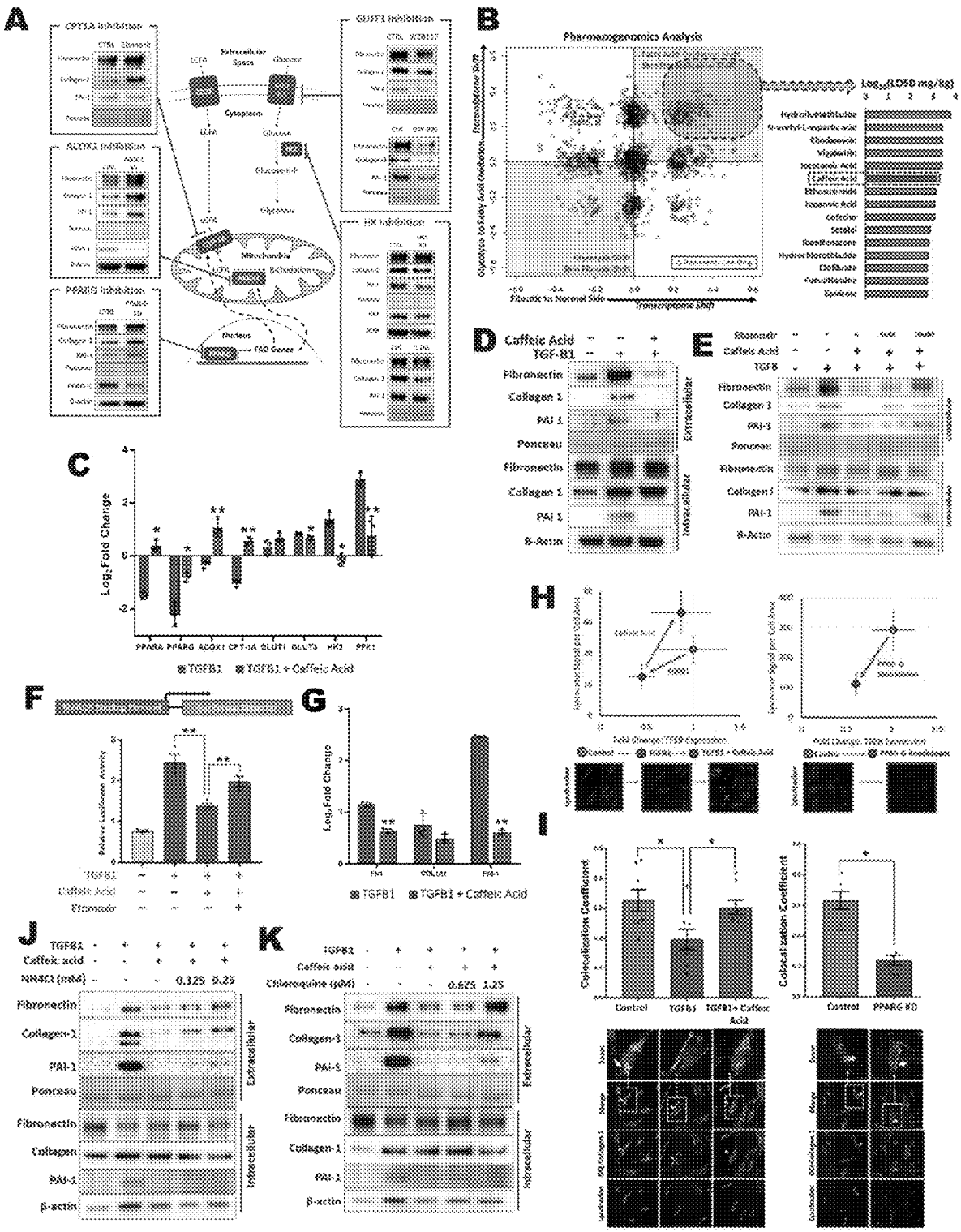
FIG. 2 shows enhancing fatty acid oxidation induces a catabolic fibroblast that downregulates ECM synthesis and enhances ECM degradation. (A) Inhibiting glycolysis or FAO has reciprocal effects in decreasing or increasing ECM proteins in dPHFs respectively. Western blot of extracellular fibronectin, collagen-1, and PAI-1. Ponceau used as loading control. Etomoxir (10 uM), WZB-117 (10 uM), BAY-876 (40 nM). HK2, ACOX1, and PPARG knockdown performed using CRISPR/Cas9. (B) Pharmacogenomics analysis identified caffeic acid as a compound that reverses metabolic alterations in skin fibrosis. The trimodal distribution for each connectivity score was due to a pattern matching strategy based on Kolmogorov-Smirnov statistic. (Left) X-axis represents drugs that shift the transcriptome in a direction from fibrotic to normal skin. Y-axis represents drugs that shift the transcriptome from glycolysis to PPAR signaling. (Right) Drugs in the top right quadrant were ranked based on lethal dose 50 (LD50 ), a measure of drug toxicity. (C) Caffeic acid reversed metabolic alterations associated with ECM accumulation in dPHFs. qRT-PCR profiling of PPAR and glycolysis genes for TGF-B1 (3 ng/ml)±caffeic acid (40 uM), relative to untreated control. n=3 per group. Pair wise fixed reallocation randomization test performed using REST. All data is expressed as mean±s.e.m. *P<0.05, **P<0.01. (D,E) Extracellular and intracellular fibronectin, collagen, and PAI-1 western blot for dPHFs treated with TGF-B1 (3 ng/ul)±caffeic acid (40 uM)±etomoxir. Ponceau and B-actin were utilized for extracellular and intracellular loading control respectively. (F) SMAD3 dependent transcription is regulated by the metabolic state of dPHFs. TGF-B1 (3 ng/ml), Caffeic acid (40 uM), Etomoxir (10 uM). n=3 per group. Values represent luciferase/Renilla activity. (G,I) One-way ANOVA. (G) Regulation of pro-fibrotic gene expression by caffeic acid in TGF-B1 stimulated fibroblasts. TGF-B1 (3 ng/ml), Caffeic acid (40 uM). n=3 per group. (H) Catabolic potential of dPHFs is regulated by FAO. (Top) X-axis represents Transcription factor EB (TFEB) expression for dPHFs relative to control. Y-axis represents lysosome signal per cell area using LysoTracker. TGF-B1 (3 ng/ml), caffeic acid (40 uM). n=3 per group. (Bottom) Representative lysotracker confocal images demonstrating alterations in lysosomal signal. (I) Collagen-1 co-localization with lysosomes is regulated by the metabolic state of dPHFs. (Top) Quantification of co-localization between lysotracker and DQ-collagen-1. (Bottom) Representative images demonstrating alterations to DQ-collagen 1 and lysotracker co-localization. TGF-B1 (3 ng/ml), caffeic acid (40 uM). (J,K) Lysosomal inhibitor $NH_4Cl$ and chloroquine regulation of extracellular and intracellular levels of fibronectin, collagen-1 and PAI-1 by western blot for caffeic acid (40 uM) treated dPHFs. Ponceau and B-actin were utilized for extracellular and intracellular loading control respectively. All data is expressed as mean±s.e.m. *P<0.05, **P<0.01.

To demonstrate that this metabolic shift directly alters the level of ECM proteins, we regulated the metabolic state of dPHFs at multiple steps in the FAO and glycolysis pathway (FIG. 2A). Inhibition of FAO in dPHFs through CRISPR/Cas9 KD of PPARG or ACOX1, or by inhibition of CPT-1A using etomoxir, resulted in an elevation in extracellular levels of fibronectin, collagen-1, and PAI-1. Conversely, suppression of glycolysis through inhibition of glucose transporters using WZB-117 and BAY-876 or inhibition of hexokinase by 2-deoxy-d-glucose (2-DG) or CRISPR/Cas9 KD of hexokinase 2 resulted in a downregulation in ECM proteins. Thus, FAO and glycolysis had antagonistic roles in regulating ECM protein levels, revealing that the balance of FAO and glycolysis in fibroblasts has an important role in ECM homeostasis.

Figure 11:
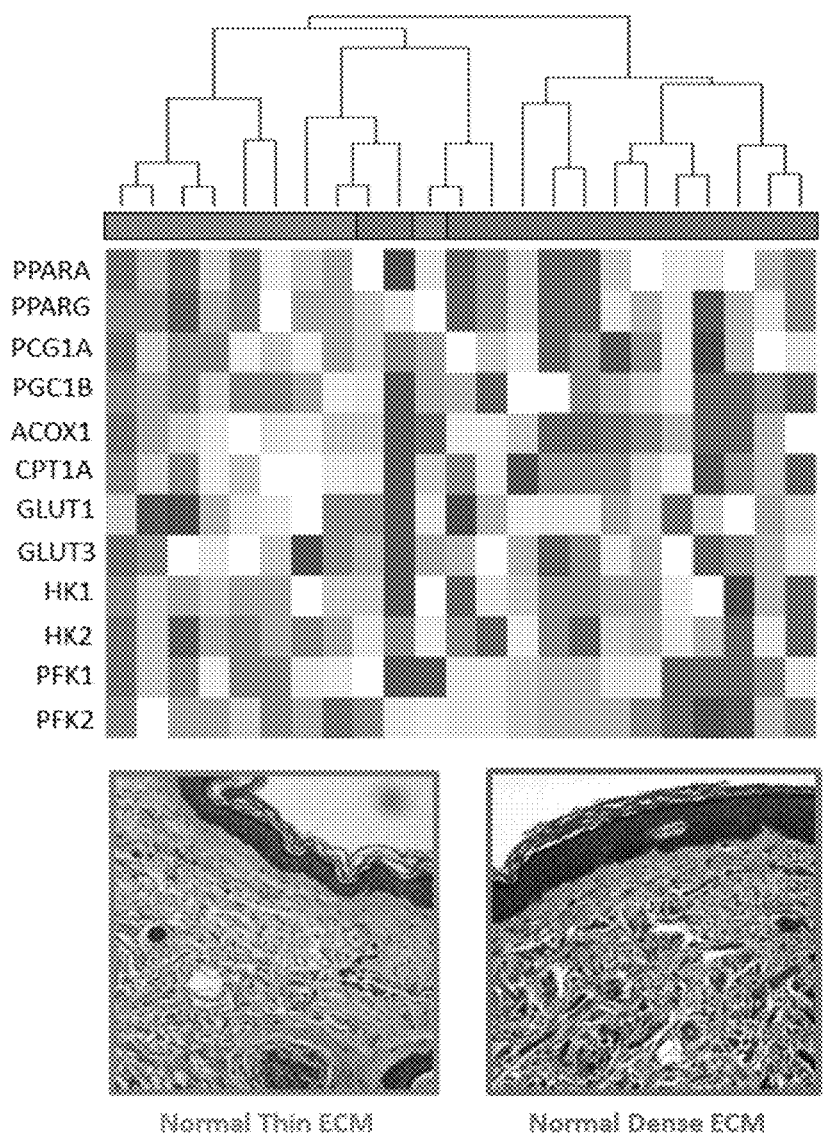
FIG. 11 shows unsupervised clustering of human skin with varying ECM accumulation based on PPAR signaling and glycolysis genes. Normal thin ECM obtained from neck skin. Normal dense ECM obtained from back or leg skin. Unsupervised hierarchical clustering segregated normal thin versus dense ECM skin based on their metabolic gene signature.
Figure 12:
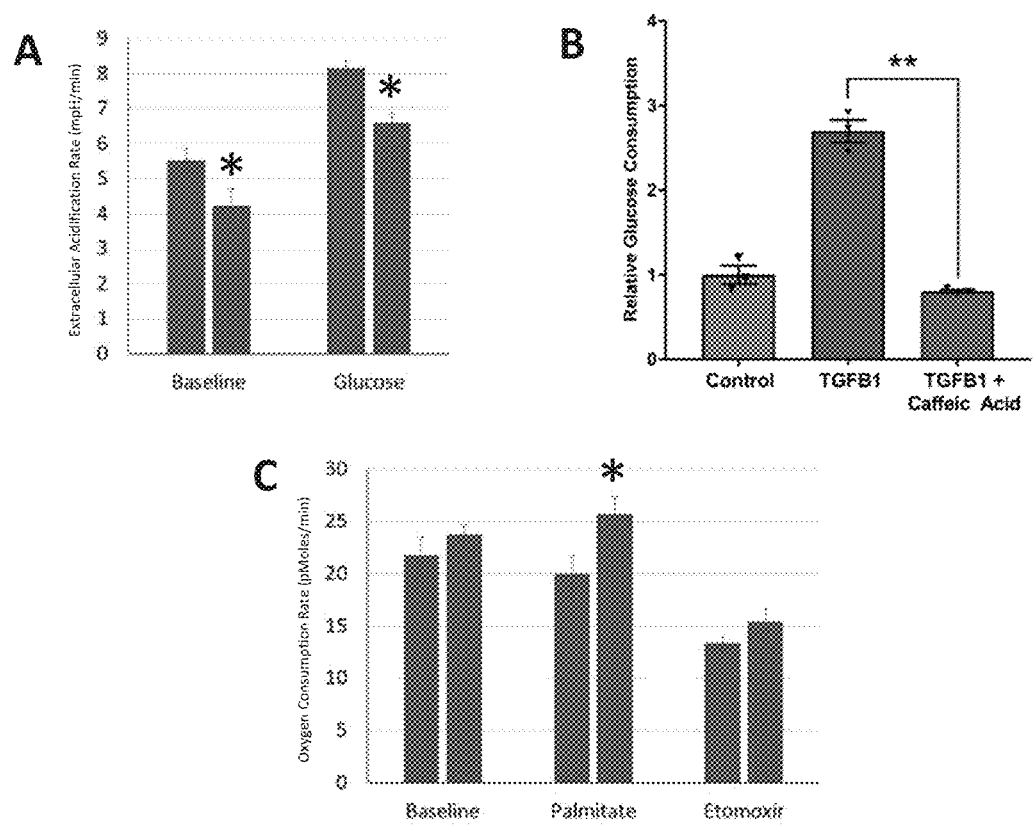
FIG. 12 shows caffeic acid functionally shifts metabolism of TGF-B1 stimulated dermal primary human fibroblasts (dPHFs) from glycolysis to fatty acid oxidation. (A) Glycolysis stress test. Extracellular acidification rate as a measure of glycolysis at baseline and with glucose (1 mM). n=14 per group. (B) Glucose consumption as calculated based on a reduction in media glucose concentrations after 24 hours of treatment and relative to control untreated cells. n=3 per group. (C) FAO for TGF-B1±caffeic acid. Y-axis represents oxygen consumption rate, a measure of metabolite oxidation over time. Palmitate (170 uM), etomoxir (40 uM) and oligomycin (2 uM). Etomoxir inhibits FAO by irreversibly binding to CPT-1A. Replicates were normalized by CyQUANT Direct Cell Proliferation Assay Kit. n=8 per group. Student's T-Test. All data is expressed as mean±s.e.m. *P<0.05.
Figure 13:
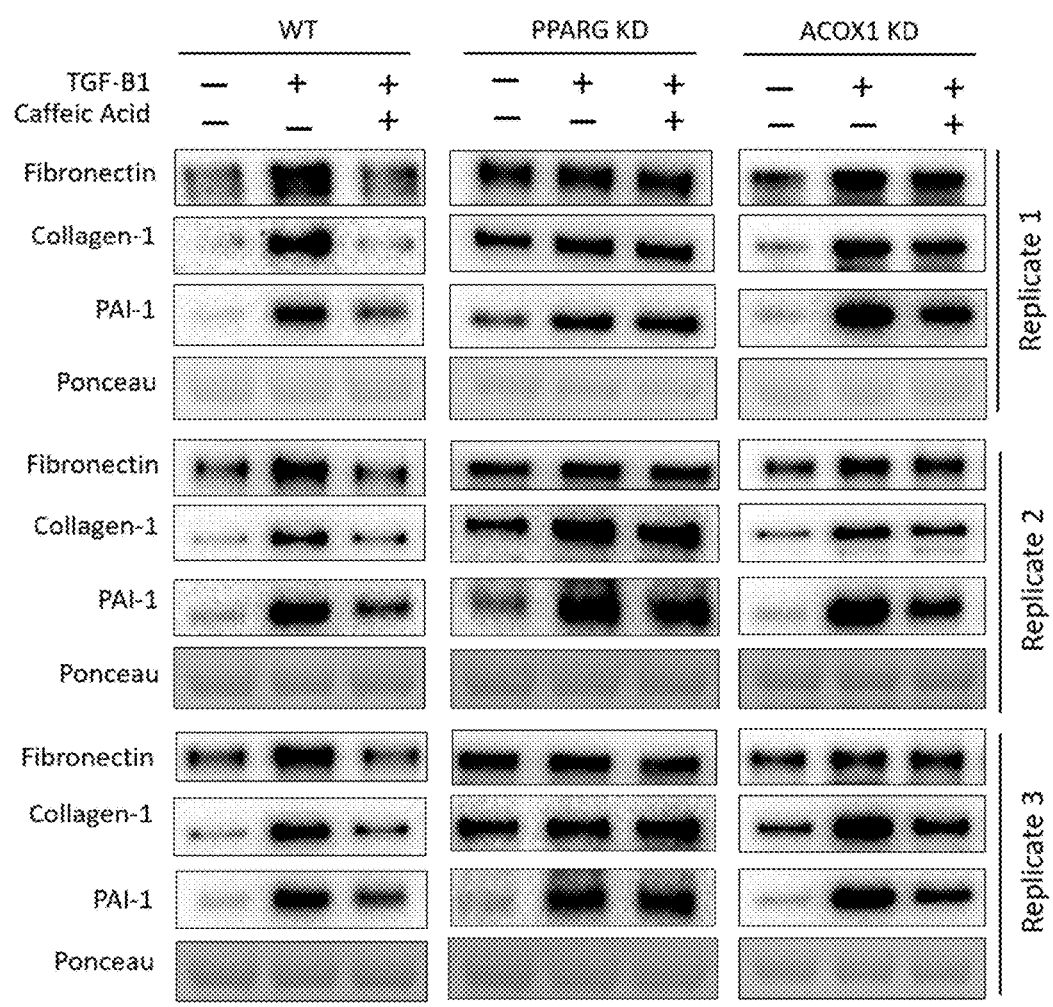
FIG. 13 shows caffeic acid acts through the PPAR pathway to downregulate ECM proteins. TGF-B1 (3 ng/ml) ±caffeic acid (40 uM) was used to treat WT cas9 control or PPARG/ACOX CRISPR/Cas9 knockdown dermal primary human fibroblasts. Supernatant was collected at 24 hours post-treatment. Ponceau used as loading control.

As these metabolic alterations may be central to cutaneous ECM regulation, we asked whether reversing the shift from FAO to glycolysis may reduce ECM accumulation. A pharmacogenomics screening approach was undertaken to uncover compounds that could satisfy two conditions: (1) shift cellular metabolism from glycolysis to FAO and (2) restore human skin fibrosis transcriptome back to normal (FIG. 2B). Connectivity map (CMAP) is a database of transcriptome profiles from human cell lines pre and post drug treatment[7]. Drugs in CMAP were assessed by these two conditions and were further filtered based on their toxicity via lethal dose 50% (LD50) and known mechanisms of action. Caffeic acid, a purported PPAR agonist, emerged as a top candidate[8]. Caffeic acid upregulated PPAR genes and downregulated glycolysis genes in TGF-B1 treated dPHFs and functionally shifted metabolism from glycolysis to FAO (FIG. 2C, FIG. 11). Caffeic acid markedly downregulated extracellular fibronectin and collagen-1, while both intracellular and extracellular PAI-1 were reduced (FIG. 2D). This effect of caffeic acid was inhibited by etomoxir, a FAO inhibitor, and was abrogated in dPHFs lacking PPARG or ACOX1, confirming that enhancing FAO is important for reducing pro-fibrotic protein levels (FIG. 2E, FIG. 12). Yet as FAO and glycolysis are competing metabolic pathways with cross-inhibition, the effect of inhibiting glycolysis with WZB-117 was examined. WZB-117 reduced extracellular fibronectin, collagen-1 and PAI-1 protein levels, even in dPHFs lacking PPARG and ACOX1 (FIG. 13). Taken together, these data suggest that enhancing FAO or suppressing glycolysis in fibroblasts directly inhibits ECM accumulation.

Figure 14:
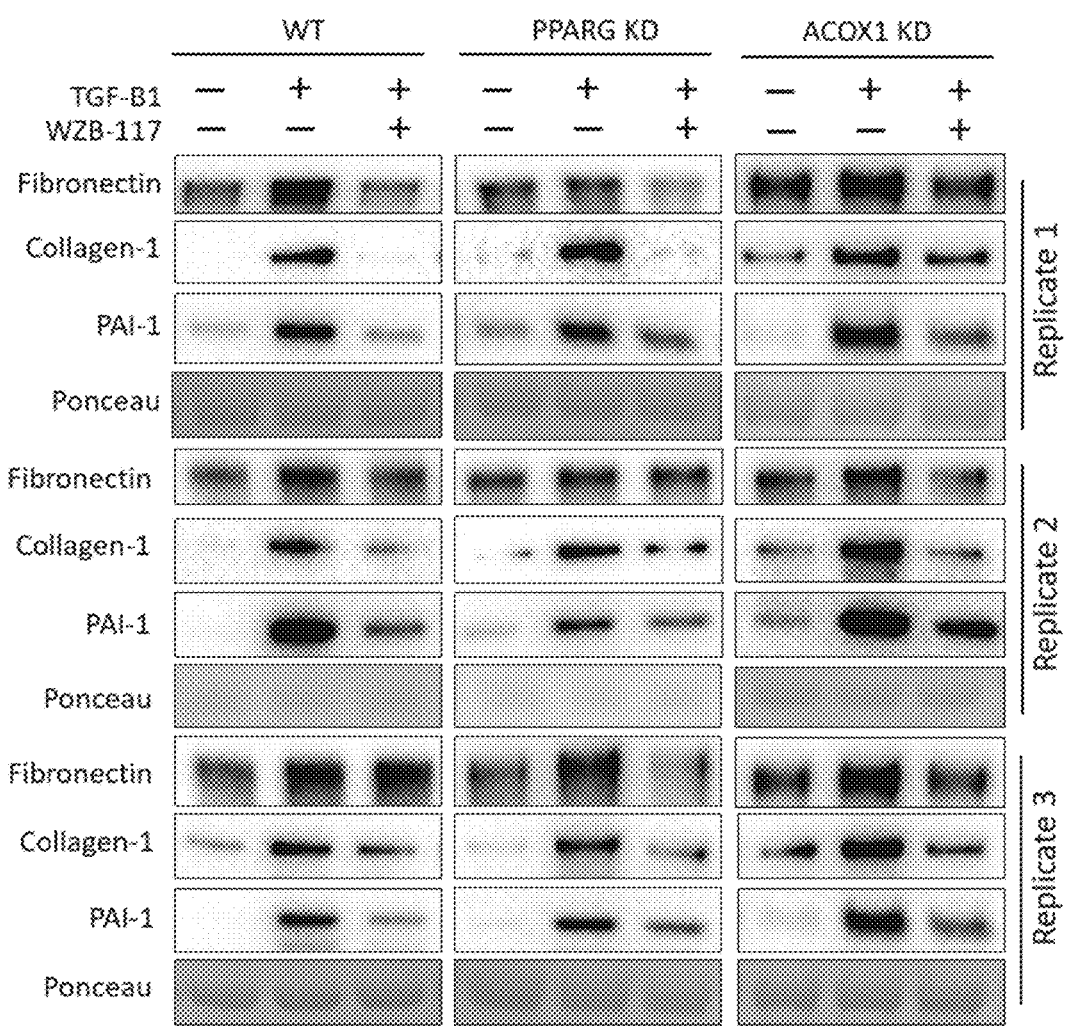
FIG. 14 shows WZB-117 inhibits ECM protein levels independent of PPAR signaling. WZB-117 is a glycolysis inhibitor acting at the level of glucose transporters (GLUT1/3). TGF-B1 (3 ng/ml)±WZB-117 (10 uM) was used to treat wildtype or PPARG/ACOX CRISPR/Cas9 knockdown dermal primary human fibroblasts. Supernatant was collected at 24 hours post-treatment.

To determine the mechanism by which a shift from glycolysis to FAO reduces ECM accumulation, alterations to both ECM synthesis and degradation were interrogated. To assess ECM synthesis, a SMAD3 driven luciferase reporter was constructed. SMAD3 is a signal transducer and transcription factor activated by multiple pro-fibrogenic cytokines; directly inducing transcription of collagen-1, fibronectin, and PAI-1[9]. Caffeic acid reduced SMAD3 dependent transcription in response to TGF-B1 and significantly downregulated the expression of PAI, while FN1 and COL1A1 were moderately decreased (FIGS. 2F,G). This effect on SMAD3 dependent transcription was inhibited by etomoxir, confirming that enhancing FAO directly reduced the transcription of ECM genes (FIG. 2F). Similarly, WZB-117 and 2-DG inhibited SMAD3 dependent transcription, but this effect was not rescued by etomoxir (FIG. 14), suggesting that primary suppression of glycolysis is also important and may, at least in part, act independently of FAO to inhibit ECM synthesis.

Interestingly, upregulation of FAO only reduced extracellular, but not intracellular collagen-1 and fibronectin (FIG. 2C). As fibroblasts have the capacity of ECM phagocytosis and lysosomal degradation, we proposed that enhancing FAO promotes ECM degradation[10]. Consistent with its anabolic role, TGF-B1 suppressed the catabolic potential of dPHFs by downregulating expression of transcription factor EB (TFEB), a master regulator of lysosomal biogenesis, and significantly decreased lysosome signal in dPHFs (FIG. 2H left). This effect was recapitulated in fibroblasts lacking PPARG, suggesting that the downregulation of PPAR signaling by TGF-B1 plays a role in reducing catabolism in dPHFs (FIG. 2H right). In agreement, upregulating FAO with caffeic acid rescued the catabolic potential of dPHFs by increasing expression of TFEB and lysosomes in dPHFs (FIG. 2H left). To determine whether these shifts in catabolism in dPHFs alters its capacity for lysosomal ECM degradation, co-localization between DQ-collagen-1, which activates fluorescence after its degradation, and lysotracker was performed (FIG. 2I). Under basal conditions, collagen-1 fluorescence was primarily detected intracellularly and co-localized with lysosomes. In the presence of TGF-B1 and with PPARG knockdown, DQ-collagen-1 was found lining the cell membrane, with almost no signal detected intracellularly, leading to a significant reduction in co-localization with lysosomes. This suggests that inhibition of FAO in dPHFs disrupts the internalization of collagen-1. Rescue of FAO in dPHFs by caffeic acid reactivated internalization of collagen-1 in dPHFs, leading to a significant increase in co-localization between DQ-collagen-1 and lysosomes. To confirm that reactivation of co-localization upregulates lysosomal ECM degradation, $NH_4Cl$ and chloroquine, two lysosomal inhibitors, were shown to inhibit the downregulation of extracellular fibronectin and collagen-1 by caffeic acid in a dose dependent manner while having no effect on intracellular levels (FIGS. 2J,2K). Interestingly, PAI-1 levels did not substantially increase with lysosomal inhibition, which combined with the large transcriptional changes to PAI-1 expression with TGF-B1 and caffeic acid (FIG. 2G), suggests that PAI-1 is more transcriptionally regulated by metabolic alterations. Taken together, shifting metabolism in fibroblasts to FAO directly antagonized the anabolic effects of glycolysis, by inducing a catabolic fibroblast phenotype that reduced ECM production and enhanced ECM degradation.

Figure 3:
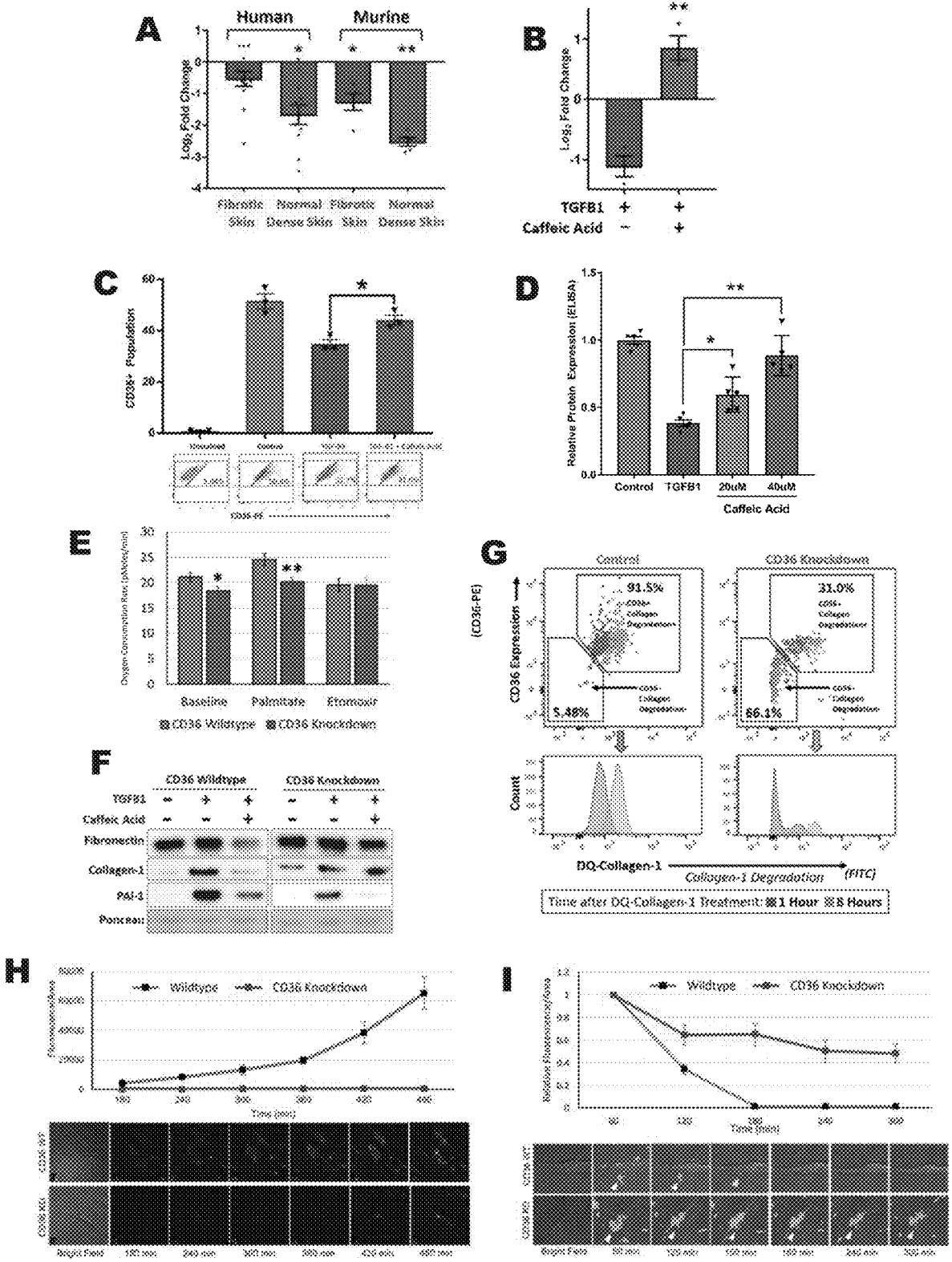
FIG. 3 shows CD36 is metabolically regulated in fibroblasts and crucial for collagen-1 degradation. (A) CD36 gene expression assessed by qRT-PCR in human and murine radiation-induced skin fibrosis and in normal skin with ECM accumulation. Relative to control or thin ECM skin. Human: n=9 control/thin ECM, n=13 skin fibrosis, n=12 dense ECM skin. Murine: n=5 control, n=7 skin fibrosis, n=5 thin ECM, n=5 dense EM. Pair wise fixed reallocation randomization test performed using REST. (B) CD36 gene expression by qRT-PCR for dPHFs treated with TGF-B1 (3 ng/ml)±caffeic acid (40 uM) relative to control. n=3 per group. One-way ANOVA. (C) CD36 surface expression by flow cytometry for dPHFs treated with TGF-B1 (3 ng/ml)±caffeic acid (40 uM). (D) FAO of CD36 wildtype and knockdown dPHFs. Palmitate (170uM), etomoxir (40 uM). n=18 per group. Student's T-Test. (E) Western blot for extracellular fibronectin, collagen-1 and PAI-1 for CD36 wildtype and knockdown dPHFs after treatment with TGF-B1 (3 ng/ml)±caffeic acid (40 uM). Ponceau used for loading control. (F) CD36 knockdown abrogates collagen-1 degradation in dPHFs. WT and CD36 KD dPHFs were treated with DQ-collagen-1, which is florescence quenched until its degradation. Cells were profiled by flow cytometry at 1 hour (red) and 8 hours (blue) after DQ-collagen-1 addition. (Top) Scatter plot of collagen-1 degradation (x-axis) and CD36 expression (y-axis) for wildtype and CD36 knockdown dPHFs (Bottom) DQ-collagen-1 fluorescence intensity as histogram for wildtype and CD36 knockdown dPHFs. (G) Live cell imaging of CD36 wildtype and knockdown collagen-1 degradation by dPHFs. DQ-collagen-1 was utilized. Top graph y-axis represents fluorescence relative to cell surface area. Bottom panel is representative images of DQ-collagen-1 fluorescence over time. n=5 per group. 2-way ANOVA<0.001. (H) Live cell imaging of CD36 wildtype and knockdown FITC-collagen-1 degradation by PHFs. FITC-collagen-1 degradation results in a decrease in fluorescence. Top graph represents quantification of fluorescence relative to time=60 min. Quantification was performed by measuring fluorescence intensity normalized to cell area. Bottom panel shows representative image of FITC-collagen-1 binding to cell (white arrow) and decreasing in fluorescence with time. n=3 per group. 2-way ANOVA<0.001.
Figure 15:
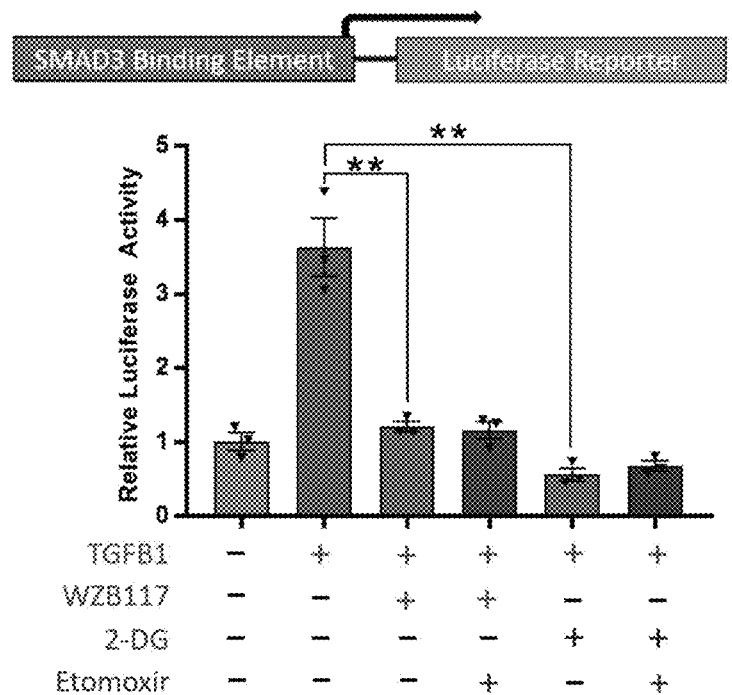
FIG. 15 shows primary suppression of glycolysis downregulates SMAD3 dependent gene transcription. Dermal primary human fibroblasts were treated with TGF-B1±WZB-117 (10 uM)±2-deoxyglucose (2-DG) (2 mM)±etomoxir (10 uM). Cells were lysed 24 hours post-treatment. Y-axis represents luciferase activity relative to renilla control. n=3 per group. One way ANOVA. n=3 per group. All data is expressed as mean±s.e.m. **P<0.01.

We next asked if there exists a surface receptor which serves as a mediator connecting the metabolic state of a fibroblast with its capacity for ECM regulation. CD36 is a transmembrane glycoprotein that imports long chain fatty acids intracellularly for FAO and is the only fatty acid transporter well known to bind components in the ECM[11]. CD36 expression was inversely correlated with ECM abundance in normal skin and was downregulated in human and murine radiation-induced skin fibrosis, all conditions demonstrated to exhibit a shift away from FAO (FIGS. 3A, 1C, 1D). Furthermore, the expression level of CD36 was found to be regulated by the metabolic state of dPHFs. FAO suppression by TGF-B1 decreased gene and surface expression of CD36 (FIGS. 3B,C, FIG. 10). Likewise, dPHFs treated with etomoxir, or with knockdown of PPARG or ACOX1, downregulated CD36 surface expression (FIG. 15). Conversely, upregulation of FAO by caffeic acid restored CD36 gene and surface expression for TGF-B1 stimulated dPHFs (FIGS. 3B,C).

Figure 16:
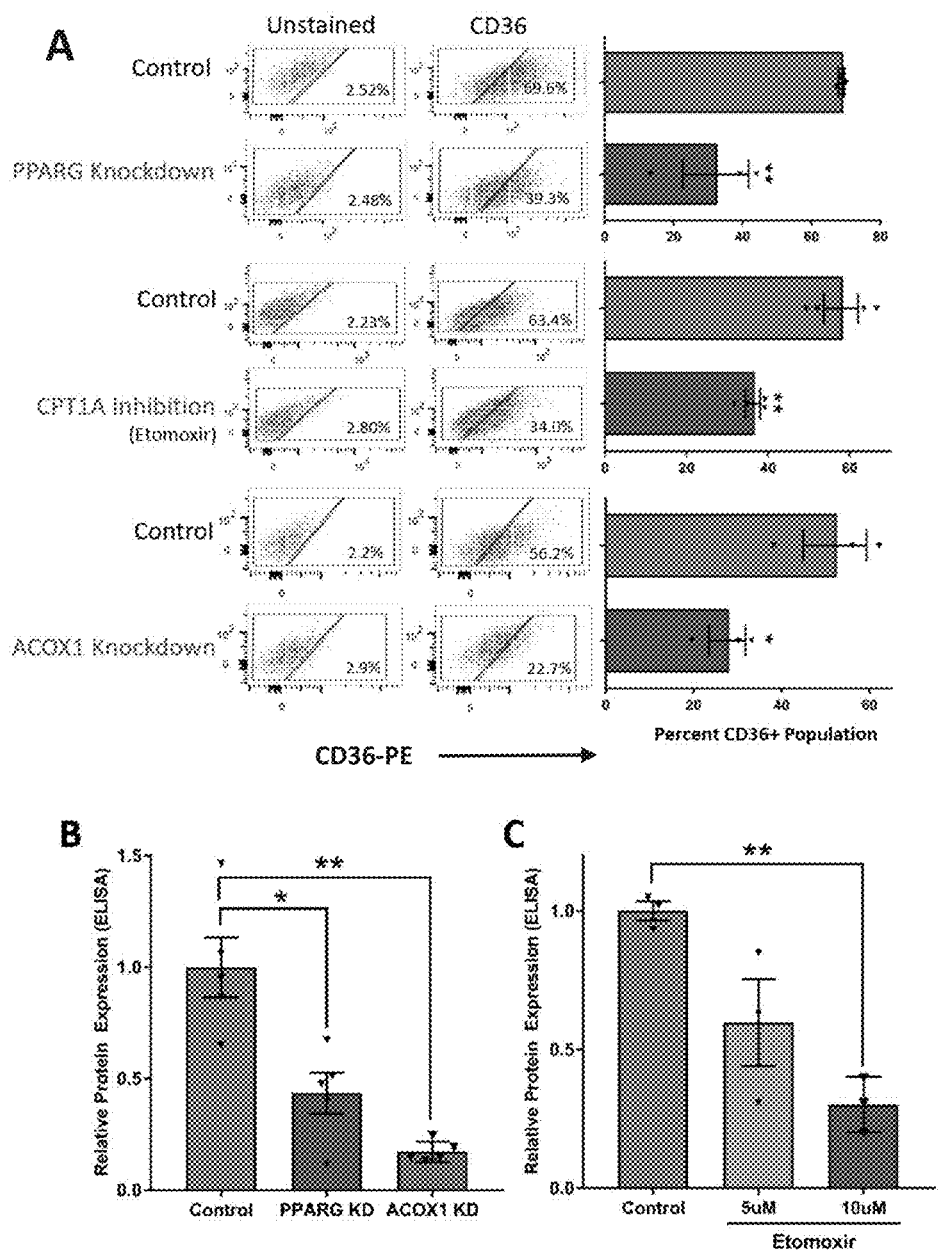
FIG. 16 shows fatty acid oxidation suppression downregulates protein levels of CD36 (A) Flow cytometry detection of CD36 in dPHFs deficient in PPARG, ACOX1, and for dPHFs treated with Etomoxir (10 uM) for 24 hours. n=3 per group for KD profiling and n=4 per group for etomoxir treatment. (B) ELISA detection of total protein level of CD36 for PPARG and ACOX1 CRISPR/Cas9 knockdown dPHFs. n=5 per group (C) ELISA detection of CD36 for etomoxir treated dPHFs. n=3 per group. Knockdown cells were profiled versus Cas9 control and Etomoxir treatment was performed in WT fibroblasts. Student's T-Test. *P<0.05. **P<0.01.

As CD36 expression correlated with the FAO status of fibroblasts, we asked whether CD36 may mediate the catabolic effects of FAO by directly promoting ECM degradation. CD36 knockdown using CRISPR/Cas9 significantly reduced the capacity of dPHFs to upregulate FAO in response to palmitate (FIG. 3D) and inhibited the capacity of caffeic acid in reducing TGF-B1 mediated upregulation of extracellular collagen-1 and fibronectin (FIG. 3E). To determine whether the degradation of extracellular collagen-1 was impaired by CD36 knockdown, DQ-collagen-1 was utilized. As assessed by flow cytometry, the majority of WT dPHFs were CD36+ and demonstrated a cumulative increase in DQ-collagen-1 degradation over 8 hours after DQ-collagen 1 treatment (FIG. 3F). CD36 knockdown enriched for a population of CD36− dPHFs with no capacity to degrade collagen-1, even after 8 hours in the presence of DQ-collagen-1 (FIG. 3F). This effect was confirmed with a second gRNA targeting CD36 (FIG. 16). Live cell imaging revealed that DQ-collagen-1 degradation occurred intracellularly in dPHFs, but was almost entirely abrogated by CD36 knockdown (FIG. 3G). To confirm the crucial role of CD36 in mediating collagen-1 degradation, FITC-collagen-1 was used which decreases in florescence with its degradation. Live cell imaging revealed that FITC-collagen-1 binds to the cell surface and over time decreases in signal intensity for WT dPHFs (FIG. 3H). CD36 knockdown did not affect FITC-collagen-1 binding to the cell surface, but significantly reduced the rate of collagen-1 degradation (FIG. 3H).

Figure 4:
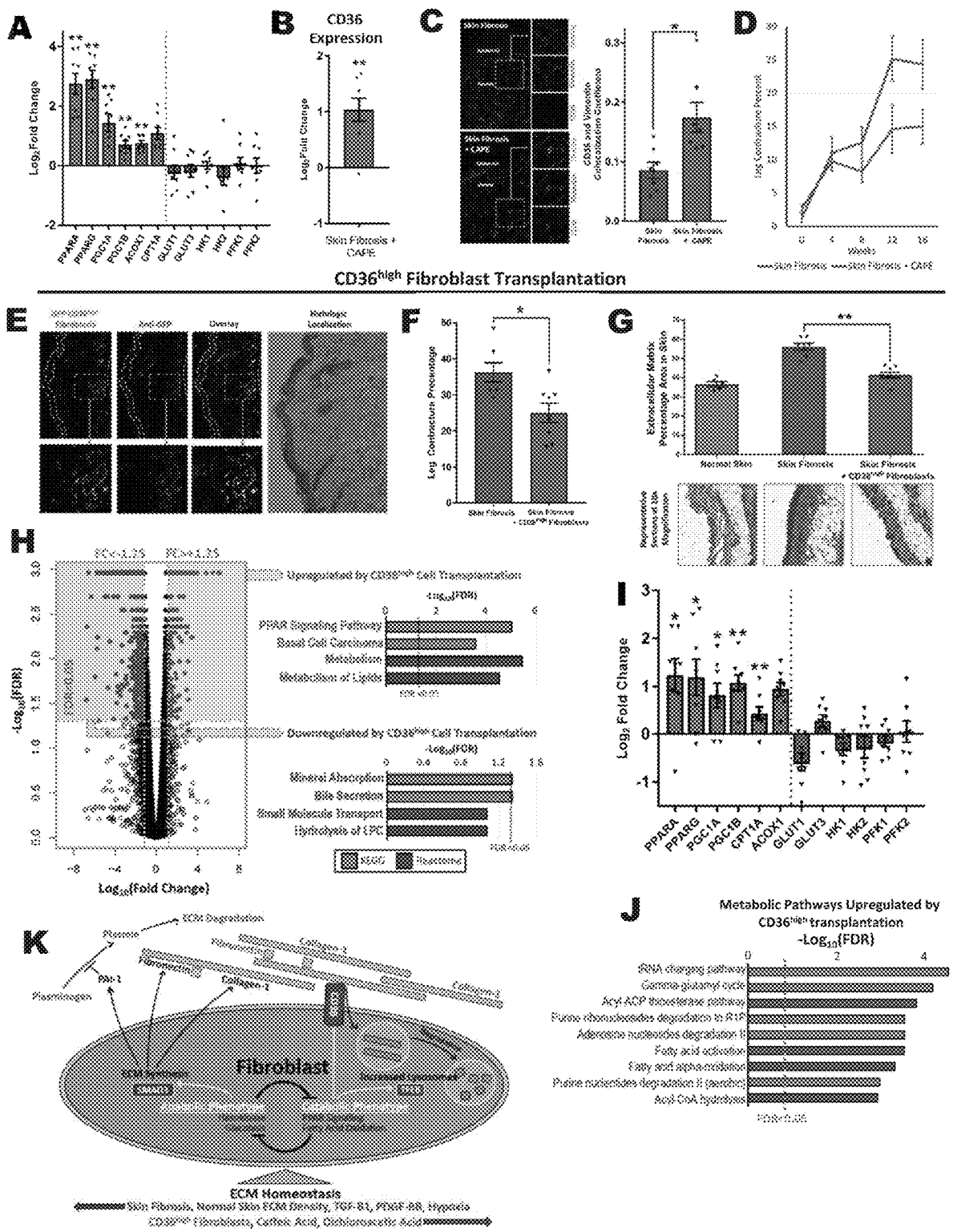
FIG. 4 shows pharmacologic and cellular therapy restores FAO/glycolysis balance in skin and reduces ECM accumulation. (A-D) Metabolic reprogramming of radiation-induced skin fibrosis using caffeic acid phenethyl ester (CAPE). Analysis performed at 16 weeks post-treatment. n=8 CAPE, n=8 vehicle (PBS). (A,B) Pair wise fixed reallocation randomization test performed using REST. (A) qRT-PCR of PPAR signaling and glycolysis expression with CAPE and vehicle treatment. Normalized to CAPE group. (B) CD36 expression assessed by qRT-PCR. (C) Co-immunofluorescence for vimentin+ (mesenchymal) cells expressing CD36 with CAPE and vehicle treatment. (D) Leg contracture for skin fibrosis with CAPE or vehicle. CAPE was delivered IP 10 mg/Kg 3 times per week for 10 weeks. 2-way ANOVA P<0.001. (E-K) Metabolic reprogramming of radiation-induced skin fibrosis using $CD36^{high}$ fibroblast transplantation. Analysis performed at 16 weeks post-treatment. (E) Localization of GFP expressing $CD36^{high}$ fibroblasts in skin fibrosis post-transplantation. Tissue collected at 7 days post-transplantation. (Left) Localization of GFP expressing CD36$^{high}$ fibroblasts was confirmed using anti-GFP/secondary Cy3. (Right) Overlay of Anti-GFP/secondary Cy3 with adjacent hematoxylin and eosin section. (F) Leg contracture at 16 weeks post-CD36$^{high}$ fibroblast transplantation. Student's T-Test. *P<0.05. (G) CD36$^{high}$ fibroblast transplantation reduces ECM deposition. (Top) Quantification of trichome sections. After trichrome staining, images were deconvoluted to obtain only the blue stain, denoting ECM. The percentage ECM in skin was calculated as the percentage blue over the entire skin area. (Bottom) Representative trichome sections. Larger images with more animals in each group is found in FIG. 19. n=5 untreated, n=8 CD36$^{high}$ fibroblast treated, n=7 vehicle (PBS) treated. 2 tailed Student's t-Test. (H) Genome-wide transcriptome profiling (RNA-seq) revealed the most significant pathways upregulated by CD36$^{high}$ fibroblasts were involved with FAO. (Left) Volcano plot of all detected genes. Genes with FDR=0 removed for clarity. The upper limit of significance using Cufflinks v2.2.1 is 1E–03 FDR. (Right) Over-representation pathway analysis of genes FDR<0.5 with log(Fold Change(FC))>1.25 or <−1.25. (I-K) Untargeted metabolomics confirmed CD36$^{high}$ fibroblasts shifts metabolism in skin fibrosis from glycolysis to FAO. n=7 CD36$^{high}$ fibroblast treated, n=6 vehicle (PBS) treated. (I) Principal component analysis showed separation of CD36$^{high}$ fibroblast vs vehicle treated skin fibrosis. (J) Specific fatty acid and glycolysis metabolites detected to be significantly regulated by CD36$^{high}$ fibroblast transplantation. (K) Over-representation pathway analysis of metabolites upregulated with CD36$^{high}$ fibroblast transplantation using MouseCyc. Red bars denote pathways involved in fatty acid oxidation. No significant metabolic pathways were downregulated with CD36$^{high}$ fibroblasts. (L) Schematic diagram showing that the balance of FAO and glycolysis in fibroblasts governs their capacity for ECM anabolism or catabolism, ultimately regulating ECM homeostasis.
Figure 17:
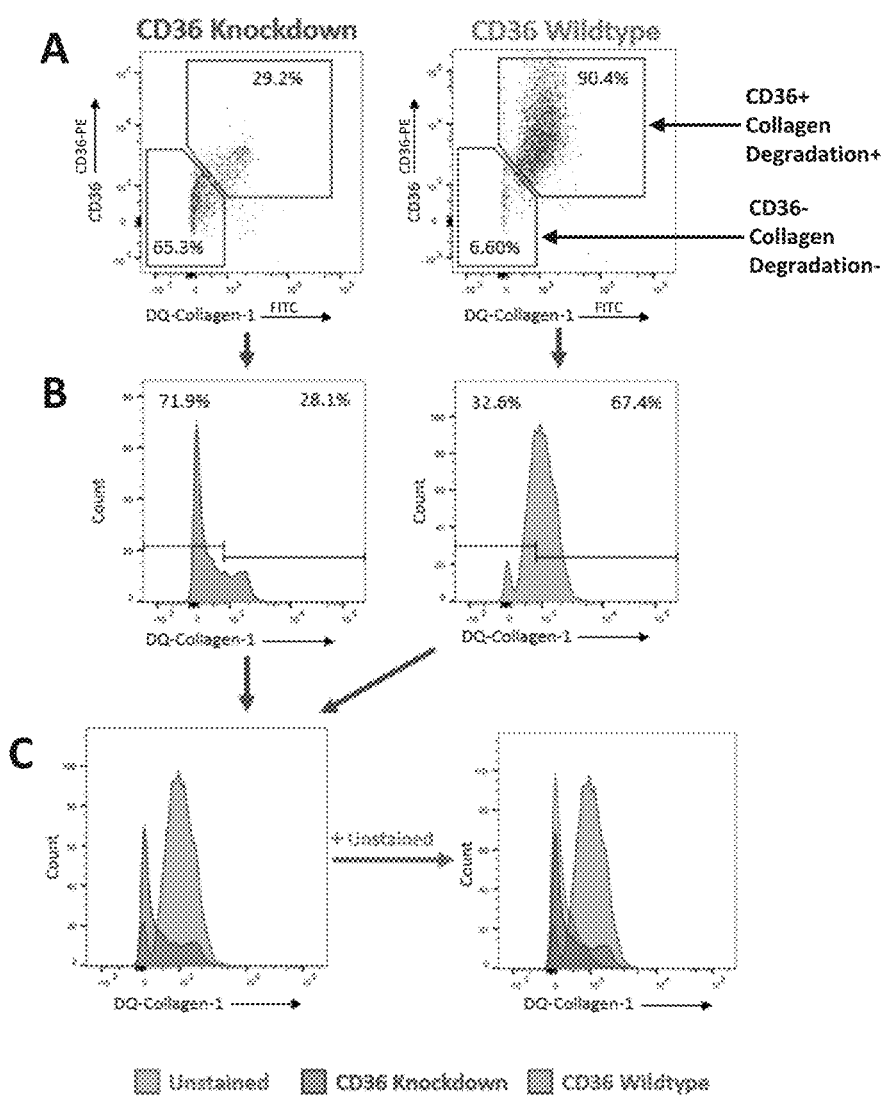
FIG. 17 shows flow cytometry detection of DQ-collagen-1 and CD36 for wildtype and second gRNA CD36 knockdown in dermal primary human fibroblasts (dPHFs). DQ-collagen-1 is fluorescence quenched and its degradation increases its fluorescence. (A) Scatter plot of CD36 expression (y-axis) and DQ-collagen-1 fluorescence (x-axis) for WT and $2^{nd}$ gRNA CD36 Crispr/Cas9 KD dPHFs. (B) Histogram plot of DQ-collagen-1 degradation. (C) (Left) Overlap of DQ-collagen-1 fluorescence for WT and CD36 KD dPHFs. (Right) Addition of unstained to emphasize enrichment of dPHFs with no collagen-1 degradation capacity due to CD36 knockdown.

To determine whether enhancing FAO may upregulate CD36 expression in vivo, mice with radiation-induced skin fibrosis were treated with caffeic acid phenethyl ester (CAPE), a more bioactive derivative of caffeic acid[12]. CAPE was confirmed to downregulate fibronectin, collagen-1 and PAI-1 in TGF-B1 treated dPHFs, and similar to caffeic acid relied on an intact PPAR pathway to exert its anti-fibrotic effects (FIG. 12). CAPE treatment in vivo upregulated PPAR signaling and the expression of CD36 in mice with skin fibrosis (FIGS. 4A,B). Co-immunofluorescence specifically demonstrated that vimentin+ (mesenchymal) cells exhibited an increase in CD36 expression with CAPE treatment (FIG. 4C). This increase in FAO and CD36 expression significantly reduced both functional and histological evidence of fibrosis severity (FIG. 4D, FIG. 17).

Figure 18:
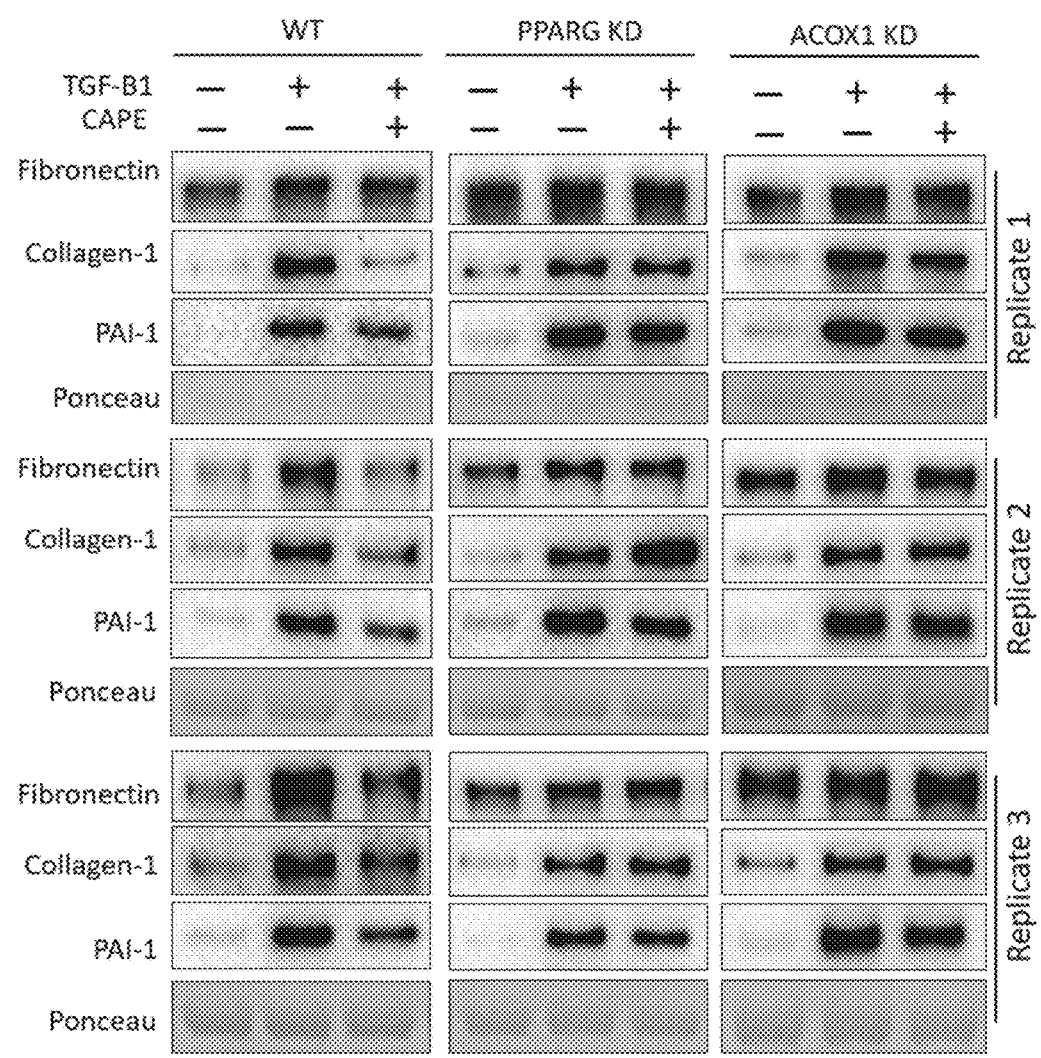
FIG. 18 shows caffeic acid phenethyl ester (CAPE) requires an intact PPAR pathway to downregulate ECM proteins. TGF-B1 (3 ng/ml)±CAPE (5 uM) was used to treat wildtype or PPARG/ACOX CRISPR/Cas9 knockdown dermal primary human fibroblasts. Supernatant was collected at 24 hours post-treatment. Ponceau used as loading control.
Figure 19:
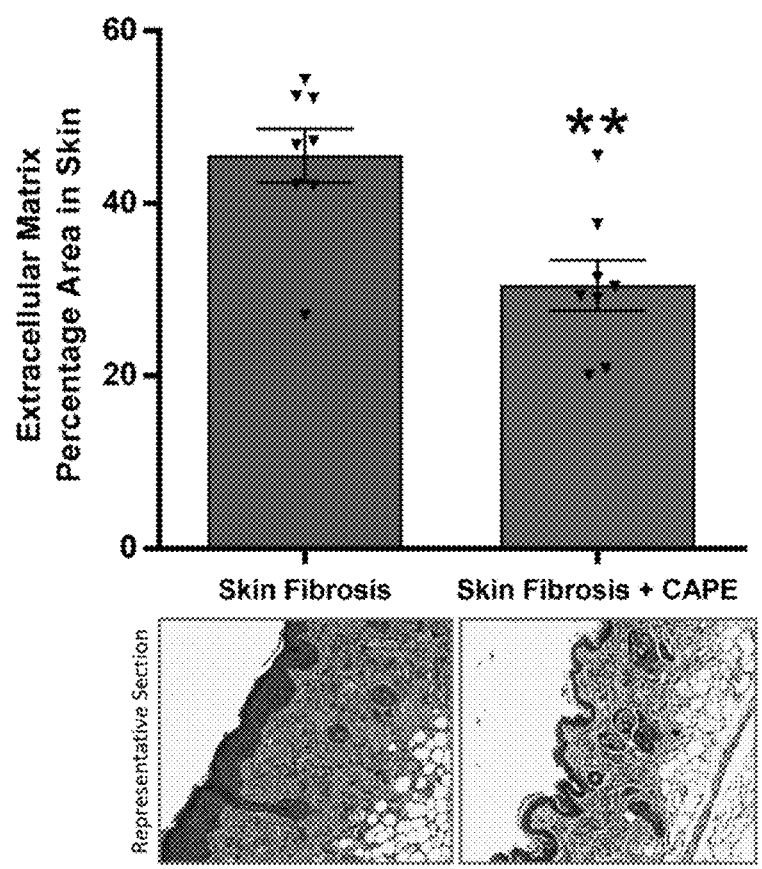
FIG. 19 shows quantification of trichrome staining through image analysis of caffeic acid phenethyl ester (CAPE) treated and vehicle control treated skin fibrosis tissue. Image color deconvolution and quantification were performed blinded to treatment groups. Bottom images are representative trichrome sections. n=8 caffeic acid, n=8 vehicle. Data are expressed as mean±s.e.m. *P<0.05 by 2-tailed student's t-Test.
Figure 20:
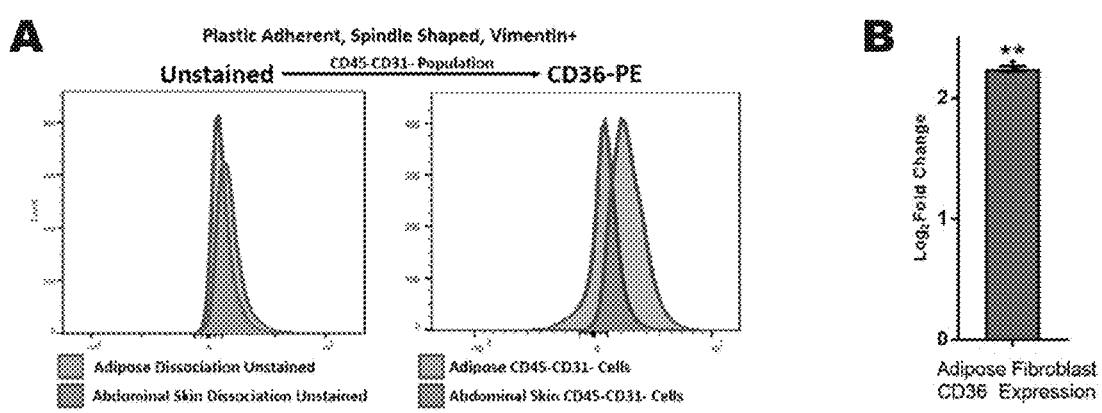
FIG. 20 shows fibroblasts derived from adipose tissue displayed significantly higher CD36 expression compared to abdominal skin fibroblasts. (A) Flow cytometry demonstrating greater CD36 surface expression on CD45–CD31– plastic adherent, spindle shaped, vimentin+ cells ($CD36^{high}$ fibroblasts) derived from adipose tissue vs. abdominal skin. (B) qRT-PCR of CD36 for abdominal vs. adipose fibroblasts. Log2 fold change relative to abdominal fibroblasts. Pair wise fixed reallocation randomization test performed using REST. All data is expressed as mean±s.e.m. **P<0.01.
Figure 21:
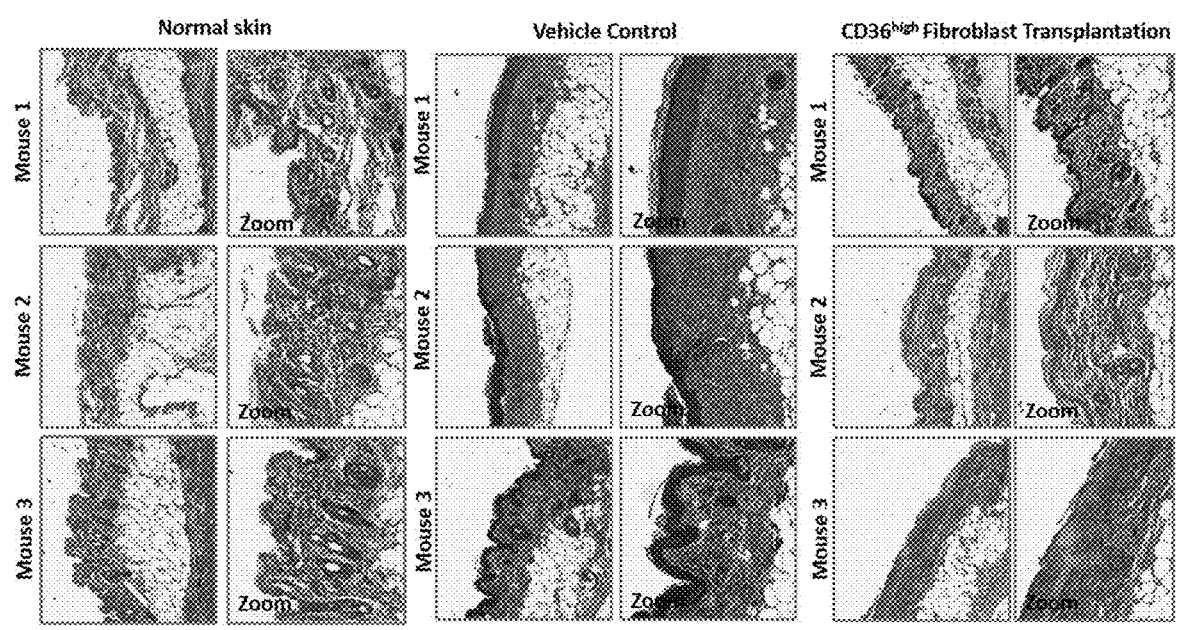
FIG. 21 shows extracellular matrix deposition in the murine skin fibrosis after $CD36^{high}$ fibroblast vs. vehicle treatment. Tissue was collected, sectioned, and trichrome stained as one batch.
Figure 22:
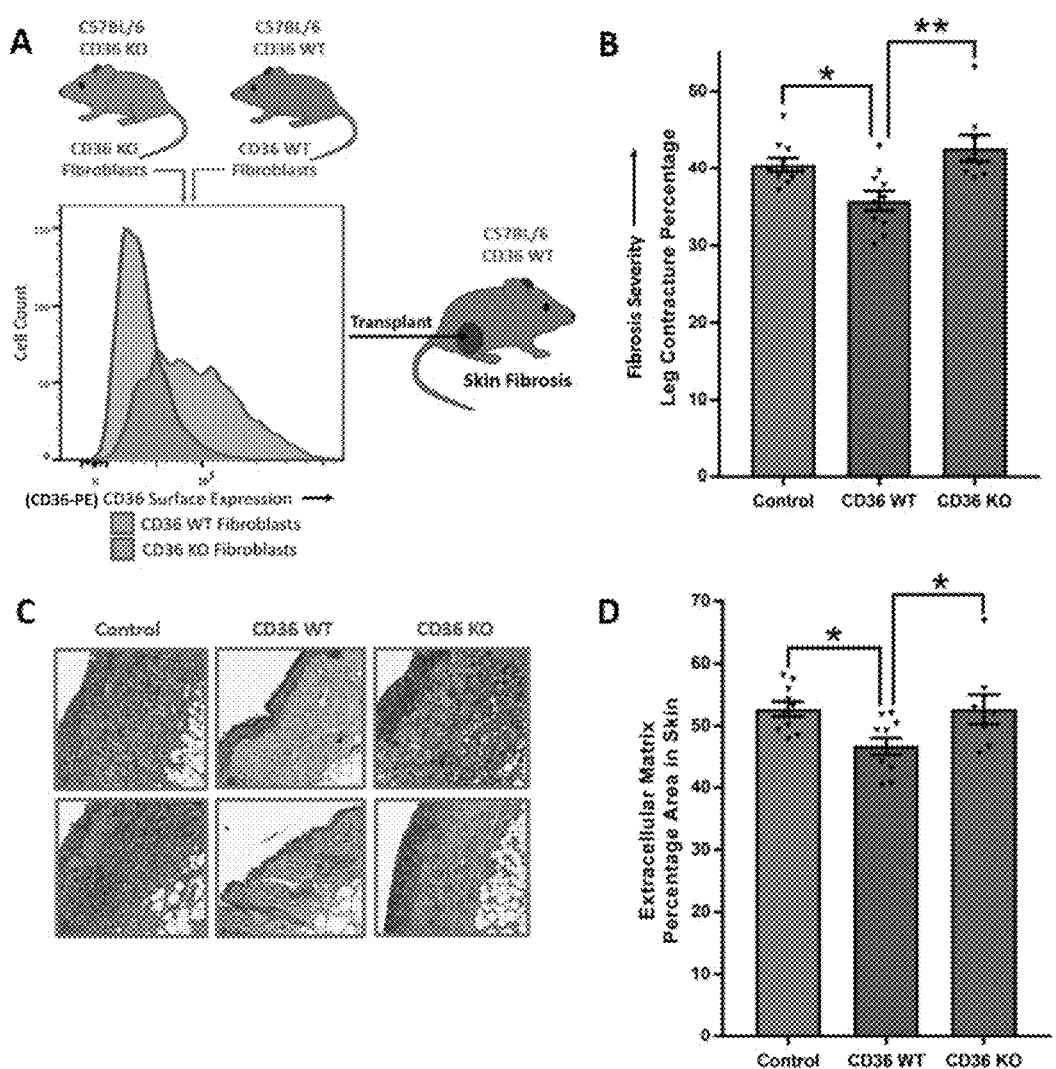
FIG. 22 shows CD36 KO adipose fibroblast transplantation did not mitigate skin fibrosis. (A) Flow cytometry confirming adipose fibroblasts isolated from CD36 KO mice lack surface expression of CD36. (B) Leg contracture for control (PBS vehicle), CD36 WT, and CD36 KO treatment of radiation induced skin fibrosis. Leg contracture was measured by two independent researchers blinded to treatment group. (C) Representative trichrome images. (D) ECM quantification in skin. Trichrome sections, all stained as one batch, were deconvoluted to only represent blue stained tissue (ECM). Area of blue over the entire area of skin was measured for each animal. n=10 PBS control, n=10 CD36 WT treated, n=8 CD36 KO treated. One way ANOVA. *P<0.05, **P<0.01.
Figure 23:
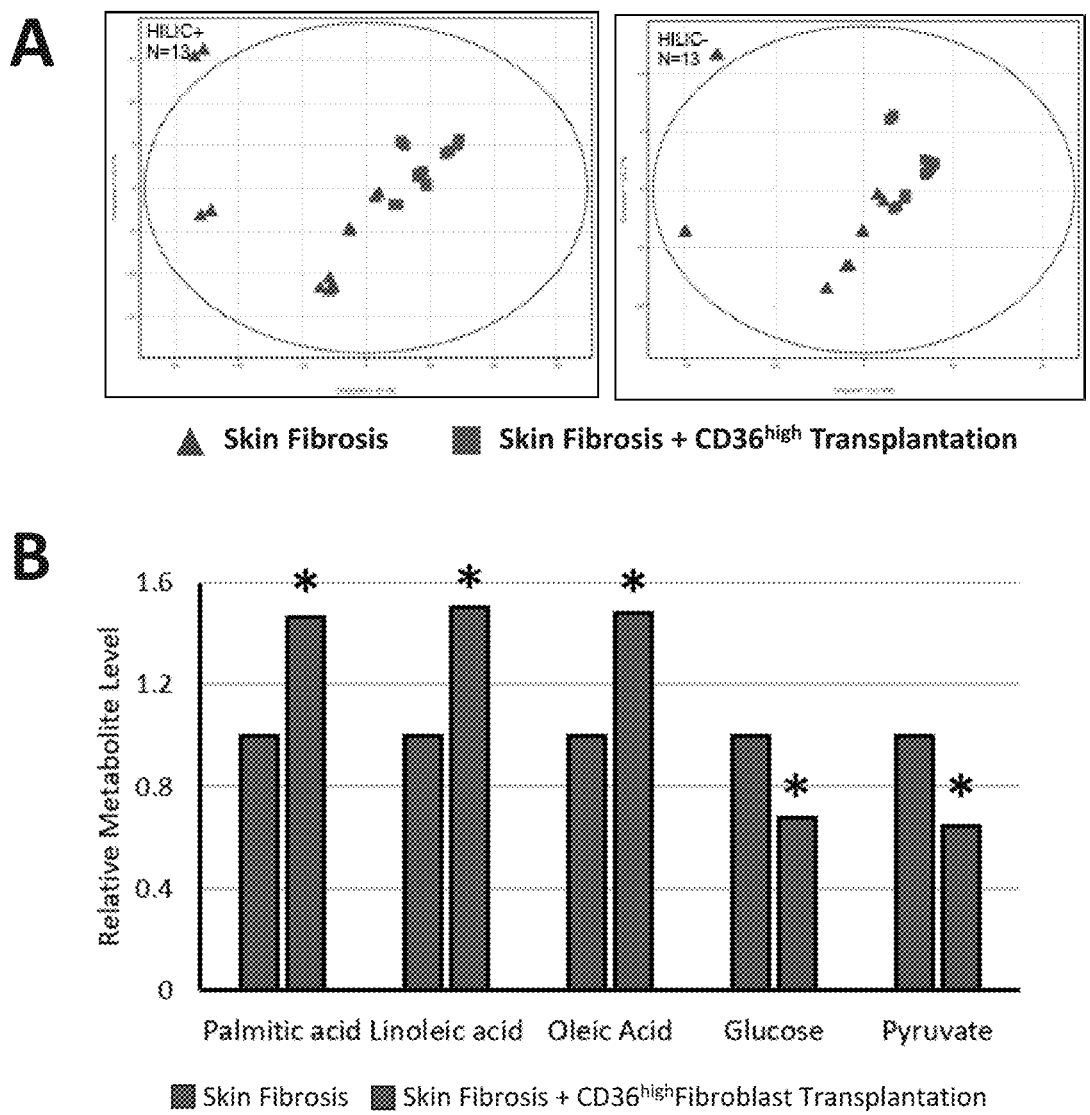
FIG. 23 shows untargeted metabolomics confirmed $CD36^{high}$ fibroblasts shifts metabolism in skin fibrosis to FAO. (A) Principal component analysis showed separation of $CD36^{high}$ fibroblast vs vehicle treated skin fibrosis. (B) Specific fatty acid and glycolysis metabolites detected to be significantly regulated by $CD36^{high}$ fibroblast transplantation. n=7 $CD36^{high}$ fibroblast treated, n=6 vehicle (PBS) treated.
Figure 24:
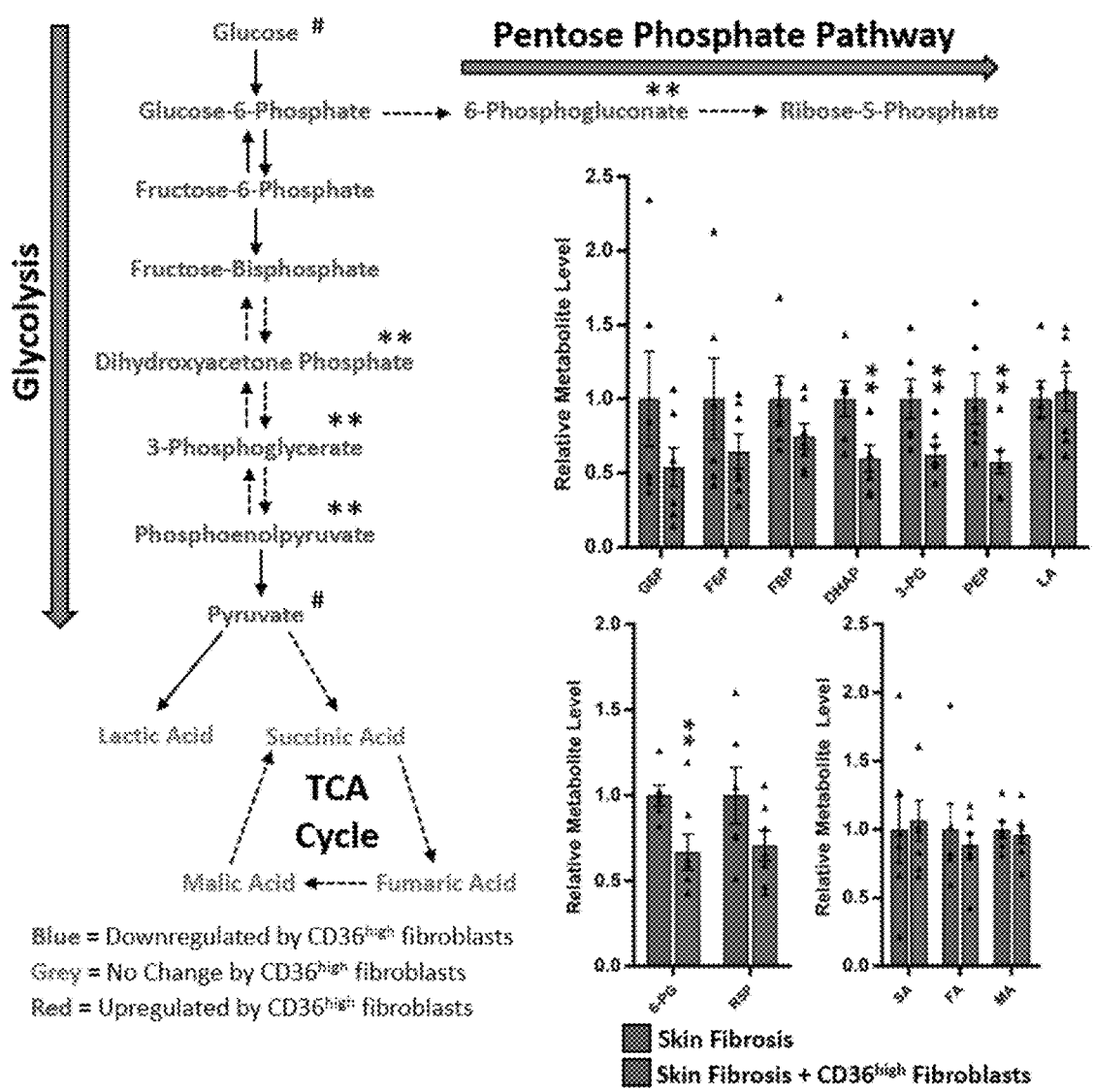
FIG. 24 shows targeted metabolite profiling of the glycolysis pathway after $CD36^{high}$ fibroblast transplantation. Glycolysis metabolites assessed by targeted metabolite profiling: G6P: glucose-6-phosphate, F6P: fructose-6-phosphate, FBP: fructose-1,6-bisphosphate, DHAP: dihydroxyacetone phosphate, 3PG: 3-phosphoglyceric acid, PEP: phosphoenolpyruvic acid, LA: lactic acid. Tricarboxylic acid (TCA) cycle metabolites. SA: succinic acid, MA: malic acid. n=7 $CD36^{high}$ fibroblast treated, n=6 vehicle treated. Student's T-test. All data is expressed as mean±s.e.m. *P<0.05, **P<0.01, #P<0.05 based on untargeted metabolomics (FIG. 23).

Given the importance of CD36 as a direct regulator of FAO and collagen-1 degradation, we asked whether transplanting fibroblasts expressing high CD36 could restore FAO/glycolysis balance and reduce skin fibrosis in vivo. One of the defining surface markers for mesenchymal cells derived from adipose tissue is their high expression of CD36. Spindle shaped, plastic adherent, vimentin+, CD45−, CD31− cells (defined herein as fibroblasts) isolated from abdominal skin and adipose tissue confirmed that CD36 surface and gene expression was highest in adipose-derived fibroblasts (FIGS. 18A,B). This population was not composed of adipocytes based on negative oil red staining. $CD36^{high}$ fibroblasts were transplanted into radiation-induced skin fibrosis and localized to the reticular dermis, a region enriched with ECM producing fibroblasts (FIG. 4E). Sixteen weeks post-transplantation, $CD36^{high}$ fibroblasts reduced collagen deposition and improved tissue elasticity (FIGS. 4F,G, FIG. 19). To confirm this effect was specific to CD36, we transplanted adipose fibroblasts isolated from CD36 KO mice, known to have a deficiency in fatty acid uptake[13], and from CD36 WT mice into the fibrotic skin of CD36 WT mice (FIG. 20). Only CD36 WT fibroblasts were capable of reducing skin fibrosis, while CD36 KO fibroblast transplantation resulted in a trend towards even greater fibrosis than vehicle control. Genome-wide transcriptome profiling and pathway analysis revealed that the most significant effect of CD36$^{high}$ fibroblast transplantation was an upregulation of the PPAR pathway and lipid metabolism (FIG. 4H), which was confirmed by qRT-PCR (FIG. 21). Untargeted metabolomics analysis confirmed that skin fibrosis treated with CD36$^{high}$ fibroblasts clustered separately from control by principal components analysis (FIG. 4I), and upregulated fatty acid metabolites, while downregulating glycolysis metabolites (FIG. 4J). Pathway analysis of significantly altered metabolites revealed multiple FAO and purine degradation pathways upregulated by CD36$^{high}$ fibroblast transplantation (FIG. 4K).

In conclusion, we have demonstrated that the balance of FAO and glycolysis may be a unifying mechanism, merging divergent molecular pathways, to govern ECM regulation in both normal and fibrotic skin (FIG. 4L). At a cellular level, regulating FAO and glycolysis shifted the phenotype of dermal fibroblasts between catabolism and anabolism. For the first time it has been shown that FAO is a driver for ECM degradation, through an upregulation of lysosomal biogenesis and an increase in surface expression of CD36, a metabolically regulated fatty acid transporter revealed to be essential for collagen-1 internalization and degradation. In support of this model, hypertrophic/keloid scarring is known to upregulate glycolysis enzymes[14]. Furthermore, caveolin-1, a scaffold protein necessary for CD36 surface expression, is reduced in fibroblasts derived from systemic sclerosis patients[15,16]. Concordantly, caveolin-1−/− mice display a scleroderma phenotype[17].

Figure 25:
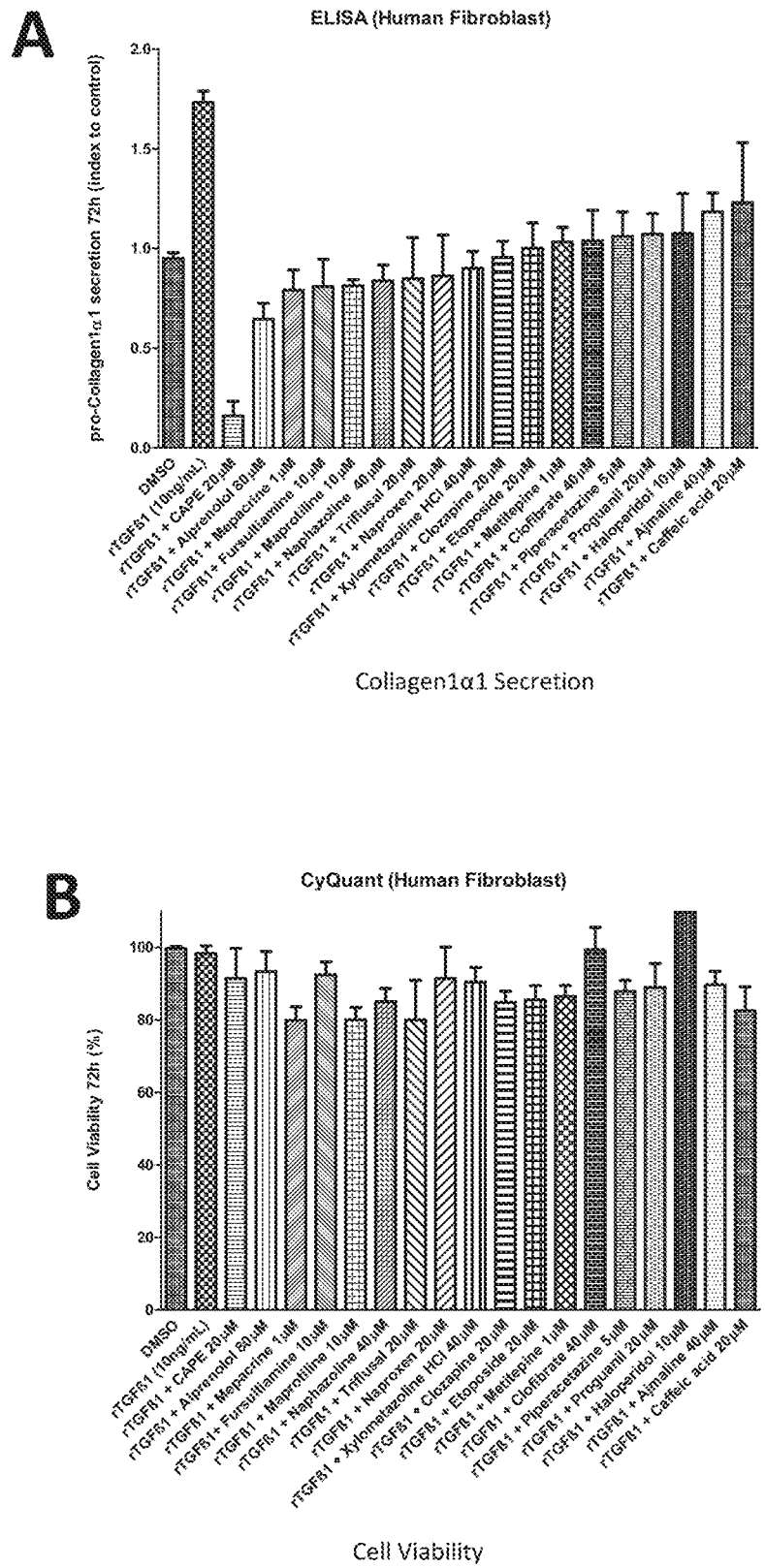
FIG. 25 shows screening of additional compounds based on pharmacogenomics screen. (A) Pro-collagen-1 ELISA screening of compounds. (B) Cyquant cell viability assay.

Utilizing this metabolic model of ECM regulation, a multitude of currently available compounds which inhibit glycolysis or upregulate FAO may play a role in the treatment of skin fibrosis, as exemplified by caffeic acid in this study. Further drug screening has been initiated to assess the utility of additional compounds found based on our pharmacogenomics screening. These compounds demonstrated the capacity to reduce collagen-1 levels, while having limited toxicity (FIG. 25). Furthermore, by uncovering CD36 as a functional surface marker for ECM degradation, future cellular therapy may be tailored for conditions requiring ECM production or degradation, based on their expression level of CD36. Finally, our metabolic model of ECM regulation may be applied to other organs, as a commonality amongst fibrosis is the activation of ECM producing mesenchymal cells. Indeed, fibroblasts isolated from patients with idiopathic pulmonary fibrosis displayed an increase in aerobic glycolysis while renal tubular epithelial cells undergoing epithelial mesenchymal transition in renal fibrosis exhibit a deficiency in FAO[18,19,20]. Therefore, shifts in glycolysis and FAO, representing metabolic alterations in anabolism and catabolism, may be a unifying phenomenon integrating upstream molecular signaling in multiple organs to control ECM homeostasis. Manipulating this metabolic balance may present exciting new therapeutic opportunities for the management of ECM regulation.

Although preferred embodiments of the invention have been described herein, it will be understood by those skilled in the art that variations may be made thereto without departing from the spirit of the invention or the scope of the appended claims. All documents disclosed herein, including those in the following reference list, are incorporated by reference.

REFERENCE LIST

1. Watt, F. M. Mammalian skin cell biology: at the interface between laboratory and clinic. *Science* 346, 937-40 (2014).

2. Vander Heiden, M. G., Cantley, L. C. & Thompson, C. B. Understanding the Warburg Effect: The Metabolic Requirements of Cell Proliferation. doi:10.1126/science.1160809

3. Kelly, B. & O'Neill, L. A. Metabolic reprogramming in macrophages and dendritic cells in innate immunity. *Cell Res.* 25, 771-784 (2015).

4. Stone, H. B., Coleman, C. N., Anscher, M. S. & McBride, W. H. Effects of radiation on normal tissue: Consequences and mechanisms. *Lancet Oncol.* 4, 529-536 (2003).

5. Kok, H. M., Falke, L. L., Goldschmeding, R. & Nguyen, T. Q. Targeting CTGF, EGF and PDGF pathways to prevent progression of kidney disease. *Nat. Rev. Nephrol.* 10, 700-711 (2014).

6. Higgins, D. F. et al. Hypoxic induction of Ctgf is directly mediated by Hif-1. *Am. J. Physiol. Renal Physiol.* 287, F1223-32 (2004).

7. Lamb, J. et al. The Connectivity Map: Using Gene-Expression Signatures to Connect Small Molecules, Genes, and Disease. *Science* (80-.). 313, 1929-1935 (2006).

8. Vanella, L. et al. Caffeic Acid Phenethyl Ester Regulates PPAR's Levels in Stem Cells-Derived Adipocytes. *PPAR Res.* 2016, (2016).

9. Isono, M., Chen, S., Hong, S. W., Iglesias-de la Cruz, M. C. & Ziyadeh, F. N. Smad pathway is activated in the diabetic mouse kidney and Smad3 mediates TGF-beta-induced fibronectin in mesangial cells. *Biochem Biophys Res Commun* 296, 1356-1365 (2002).

10. McCulloch, C. A. G. & Knowles, G. C. Deficiencies in collagen phagocytosis by human fibroblasts in vitro: A mechanism for fibrosis? *J. Cell. Physiol.* 155, 461-471 (1993).

11. Febbraio, M., Hajjar, D. P. & Silverstein, R. L. CD36: a class B scavenger receptor involved in angiogenesis, atherosclerosis,inflammation, and lipid metabolism. *J.Clin..Invest.* 108, 785-791 (2001).

12. Zhang, P., Tang, Y., Li, N.-G., Zhu, Y. & Duan, J.-A. Bioactivity and chemical synthesis of caffeic acid phenethyl ester and its derivatives. *Molecules* 19, 16458-76 (2014).

13. Coburn, C. T. et al. Defective uptake and utilization of long chain fatty acids in muscle and adipose tissues of CD36 knockout mice. *J. Biol. Chem.* 275, 32523-32529 (2000).

14. Vincent, A. S. et al. Human skin keloid fibroblasts display bioenergetics of cancer cells. *J. Invest. Dermatol.* 128, 702-709 (2008).

15. Ring, A., Le Lay, S., Pohl, J., Verkade, P. & Stremmel, W. Caveolin-1 is required for fatty acid translocase (FAT/CD36) localization and function at the plasma membrane of mouse embryonic fibroblasts. *Biochim. Biophys. Acta—Mol. Cell Biol. Lipids* 1761, 416-423 (2006).

16. Del Galdo, F. et al. Decreased expression of caveolin 1 in patients with systemic sclerosis: crucial role in the pathogenesis of tissue fibrosis. *Arthritis Rheum.* 58, 2854-65 (2008).

17. Castello-Cros, R. et al. Scleroderma-like properties of skin from caveolin-1-deficient mice: implications for new treatment strategies in patients with fibrosis and systemic sclerosis. *Cell Cycle* 10, 2140-2150 (2011).

18. Xie, N. et al. Glycolytic reprogramming in myofibroblast differentiation and lung fibrosis. *Am. J. Respir. Crit. Care Med.* 192, 1462-1474 (2015).

19. Kang, H. M. et al. Defective fatty acid oxidation in renal tubular epithelial cells has a key role in kidney fibrosis development. *Nat. Med.* 21, 37-46 (2014).

20. Lovisa, S., Zeisberg, M. & Kalluri, R. Partial Epithelial-to-Mesenchymal Transition and Other New Mechanisms of Kidney Fibrosis. *Trends in Endocrinology and Metabolism* 27, 681-695 (2016).

21. Stone, H. B. Leg contracture in mice: an assay of normal tissue response. *Int. J. Radiat. Oncol. Biol. Phys.* 10, 1053-1061 (1984).

22. Trapnell, C. et al. Differential gene and transcript expression analysis of RNA-seq experiments with TopHat and Cufflinks. *Nat. Protoc.* 7, 562-578 (2012).

23. Dutta, T. et al. Concordance of changes in metabolic pathways based on plasma metabolomics and skeletal muscle transcriptomics in type 1 diabetes. *Diabetes* 61, 1004-1016 (2012).

24. Pfaffl, M. W. Relative expression software tool (REST (C)) for group-wise comparison and statistical analysis of relative expression results in real-time PCR. *Nucleic Acids Res.* 30, 36e-36 (2002).

25. Ran, F. A. et al. Genome engineering using the CRISPR-Cas9 system. *Nat Protoc* 8, 2281-2308 (2013).

26. Dennler, S. et al. Direct binding of Smad3 and Smad4 to critical TGF beta-inducible elements in the promoter of human plasminogen activator inhibitor-type 1 gene. *EMBO J.* 17, 3091-100 (1998).

27. Irizarry, R. A. Exploration, normalization, and summaries of high density oligonucleotide array probe level data. *Biostatistics* 4, 249-264 (2003).

28. Smirnov, P. et al. PharmacoGx: An R package for analysis of large pharmacogenomic datasets. *Bioinformatics* 32, 1244-1246 (2016).

29. Rousseeuw, P. J. Silhouettes: A graphical aid to the interpretation and validation of cluster analysis. *J. Comput. Appl. Math.* 20, 53-65 (1987).

The invention claimed is:

1. A method of treating a disease associated with extracellular matrix (ECM) accumulation in a patient, the method comprising administering to the patient a therapeutically effective amount of an agent capable of shifting ECM homeostasis from glycolysis to fatty acid oxidation (FAO), wherein the disease is skin fibrosis and the agent comprises caffeic acid or caffeic acid phenethyl ester (CAPE).

2. The method of claim 1, wherein the agent further comprises sirolimus, mepacrine, benzamil, benzethonium chloride, methylergometrine, lovastatin, hydroflumethiazide, maprotiline, mifepristone, tonzonium bromide, clofibrate, fluvastatin, dihydroergocristine, clindamycin, bromocriptine, flavoxate, ajmaline, etacrynic acid, co-dergocrine mesilate, loperamide, rofecoxib, N-acetyl-L-aspartic acid, metitepine, chlortetracycline, arcaine, viomycin, (−)-isoprenaline, piperacetazine, diperodon, oxymetazoline, fursultiamine, finasteride, lactobionic acid, proguanil, levobunolol, sotalol, lithocholic acid, hydrastinine, etoposide, canadine, depudecin, cinchonidine, levocabastine, haloperidol, amiloride, proxymetacaine, harpagoside, clozapine, diflorasone, arachidonic acid, hemicholinium, fipexide, 10-ethoxyharmalan, sulmazole, azlocillin, amprolium, metixene, alprenolol, altretamine, hydroxyzine, ethosuximide, heliotrine, bromperidol, atracurium besilate, S-propranolol, pseudopelletierine, butamben, anabasine, ampyrone, homosalate, triflusal, xylometazoline, naphazoline, iopanoic acid, letrozole, isocarboxazid, vigabatrin, epirizole, quinethazone, iocetamic acid, hydrochlorothiazide, naproxen, ramifenazone, chlormezanone, atractyloside, cefaclor, cinchonine, or a combination thereof.

3. The method of claim 1, wherein the agent further comprises hydroflumethiazide, N-acetyl-L-aspartic acid, clindamycin, vigabatrin, iocetamic acid, ethosuximide, iopanoic acid, cefaclor, sotalol, ramifenazone, hydrochlorothiazide, clofibrate, fursultiamine, epirizole, chlormezanone, naproxen, (−)-isoprenaline, triflusal, finasteride, co-dergocrine mesilate, ampyrone, altretamine, heliotrine, cinchonidine, chlortetracycline, sulmazole, etacrynic acid, bromperidol, cinchonine, atractyloside maprotiline, isocarboxazid, S-propranolol, canadine, or a combination thereof.

4. The method of claim 1, wherein the skin fibrosis is radiation induced skin fibrosis.

\* \* \* \* \*